(12) United States Patent
Forrow et al.

(10) Patent No.: US 8,431,000 B2
(45) Date of Patent: Apr. 30, 2013

(54) BIOSENSOR

(75) Inventors: Nigel John Forrow, Abingdon (GB); Xiang Cheng Zhang, Abingdon (GB); Catherine Ann McTigue, Kennington (GB)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/344,324

(22) Filed: Jan. 5, 2012

(65) Prior Publication Data

US 2012/0216936 A1    Aug. 30, 2012

Related U.S. Application Data

(63) Continuation of application No. 12/815,171, filed on Jun. 14, 2010, now Pat. No. 8,101,064, which is a continuation of application No. 11/839,037, filed on Aug. 15, 2007, now Pat. No. 7,754,059, which is a continuation of application No. 10/448,643, filed on May 30, 2003, now Pat. No. 7,311,812.

(51) Int. Cl.
*G01N 27/327* (2006.01)

(52) U.S. Cl.
USPC .............. 204/403.05; 204/403.06; 204/403.1

(58) Field of Classification Search ............ 204/403.01–403.15; 205/777.5, 778, 792
See application file for complete search history.

(56) References Cited

U.S. PATENT DOCUMENTS

| | | |
|---|---|---|
| 4,399,686 A | 8/1983 | Kindlund et al. |
| 4,657,959 A | 4/1987 | Bryan et al. |
| 5,141,868 A | 8/1992 | Shanks et al. |
| 5,558,834 A | 9/1996 | Chu et al. |
| 5,628,890 A | 5/1997 | Carter et al. |
| 5,795,774 A | 8/1998 | Matsumoto et al. |

(Continued)

FOREIGN PATENT DOCUMENTS

| | | |
|---|---|---|
| EP | 0170375 | 5/1990 |
| WO | WO 96/30431 | 10/1996 |

(Continued)

OTHER PUBLICATIONS

Hench, L.L. et al., "Biomaterials—an Interfacial Approach," Academic Press, pp. 8-17, 1982.

(Continued)

*Primary Examiner* — Alex Noguerola
(74) *Attorney, Agent, or Firm* — Edward J. Baba; Daniel G. Stoddard; Bozicevic, Field & Francis LLP

(57) ABSTRACT

A biosensor for determining the concentration of an analyte in a biological sample. The biosensor comprises a support, a reference electrode or a counter electrode or both disposed on the support, a working electrode disposed on the support, the working electrode spaced apart from the other electrode or electrodes on the support, a covering layer defining a sample chamber over the electrodes, an aperture in the covering layer for receiving a sample, and at least one layer of mesh in the sample chamber between the covering layer and the electrodes. The at least one layer of mesh has coated thereon a silicone surfactant. Certain silicone surfactants are as effective as fluorinated surfactants with respect to performance of biosensors. These surfactants, when coated onto the mesh layer of the biosensor, are effective in facilitating the transport of aqueous test samples, such as blood, in the sample chamber.

19 Claims, 13 Drawing Sheets

U.S. PATENT DOCUMENTS

| | | | |
|---|---|---|---|
| 5,964,993 | A | 10/1999 | Blubaugh, Jr. et al. |
| 6,436,256 | B1 | 8/2002 | Williams et al. |
| 6,544,474 | B2 | 4/2003 | Douglas |
| 7,311,812 | B2 | 12/2007 | Forrow et al. |
| 7,754,059 | B2 * | 7/2010 | Forrow et al. ............ 204/403.05 |
| 2003/0217918 | A1 | 11/2003 | Davies et al. |

FOREIGN PATENT DOCUMENTS

| | | |
|---|---|---|
| WO | WO 98/13685 | 4/1998 |
| WO | WO 99/13100 | 3/1999 |
| WO | WO 99/19507 | 4/1999 |

OTHER PUBLICATIONS

Hoffman, P., "Project: Union Carbide SILWET Surfactant Encyclopedia," downloaded May 13, 2006 from www.digitalspaceart.com.

Kamath, Y.K. et al. "The Wicking Kinetics of Liquied Droplets into Yarns," Textile Research Journal 71, 862-69, 2001.

Kamath, Y.K. et al. "Wicking of Spin Finishes and Related Liquids into Continuous Filament Yarns," Textile Research Journal, 64, 33-40, 1994.

Kirk Othmer, Encyclopedia of Polymer Science and Technology, vol. 15, John Wiley & Sons, pp. 204-209, 234-265, 1989.

PCT Search Report for International Application No. PCT/US2004106172, mailed Oct. 13, 2004.

Perry, D. "Silicone Surface-Active Agents," Dow Corning Corp. Publication, 2005.

Petarch Catalog of Silanes, Silicones and Homogenous Catalysts pp. 150-155, 2000.

Technical Bulletin, TB100, A Bibliography of Contact Angle Use in Surface Science, ramé-hart, inc., date unknown.

* cited by examiner

Uncoated mesh

Mesh coated with alternative surfactant

Mesh coated with FC-170C (a) NY151 (0.09% DC 193), NY64 (0.35% DC 193)

(a) NY151 (0.09% DC 193), NY64 (0.35% DC 193)

(b) NY151 (0.09% DC 193), NY64 (1.05% DC 193)

(b) NY151 (0.09% DC 193), NY64 (1.05% DC 193)

BIOSENSOR

REFERENCE TO RELATED APPLICATIONS

This application is a continuation application of U.S. Patent Application Ser. No. 12/815,171, filed on Jun. 14, 2010, now U.S. Pat. No. 8,101,064, which is a continuation of 11/839,037, filed on Aug. 15, 2007, now U.S. Pat. No. 7,754,059, which is a continuation of U.S. Patent Application Ser. No. 10/448,643, filed on May 30, 2003, now U.S. Pat. No. 7,311,812, which are incorporated herein by reference in their entirety.

BACKGROUND OF THE INVENTION

1. Field of the Invention

This invention relates to biosensors. More particularly, this invention relates to biosensors in which the biological sample is transported to a sample chamber by means of wicking of fluid.

2. Discussion of the Art

A biosensor is a device for measuring the concentration of an analyte in a biological sample. A typical biosensor comprises a support, a reference electrode or a counter electrode or both a reference and a counter electrode disposed on the support, a working electrode disposed on the support, the working electrode spaced apart from the other electrode or electrodes on the support, a covering layer defining an enclosed space over the electrodes, an aperture in the covering layer for receiving a sample, and at least one mesh layer in the enclosed space between the covering layer and the electrodes. The working electrode includes an enzyme capable of catalyzing a reaction involving a substrate for the enzyme and a mediator capable of transferring electrons between the enzyme-catalyzed reaction and the working electrode to create a current related to the activity of the enzyme and related to the concentration of the analyte in the sample. Alternatively, instead of an enzyme, the working electrode can include a substrate capable of catalyzing a reaction involving an enzyme for the substrate and a mediator capable of transferring electrons between the substrate-catalyzed reaction and the working electrode to create a current related to the activity of the substrate and related to the concentration of the analyte in the sample. The purpose of the mesh layer or mesh layers is to define a path for directional flow of the sample from the aperture through the enclosed space towards the electrodes and control the height of the enclosed space above the electrodes. The mesh layers are formed of a woven material and coated with a surfactant. An example of a biosensor is shown in U.S. Pat. No. 5,628,890, incorporated herein by reference.

The test sample is required to be delivered rapidly and uniformly from a sample application zone, i.e., at the aperture, to a reaction zone within the enclosed space, which is referred to herein as a sample chamber. Typically, delivery of the test sample is carried out by wicking along the mesh layer, which is typically of a hydrophilic character for biological samples. See U.S. Pat. No. 5,628,890, EP 0170375, U.S. Pat. No. 5,141,868, and U.S. Pat. No. 6,436,256. Sample chambers of biosensors are preferably constructed so that they have a small volume for the purpose of reducing the amount of test sample (generally blood) required from a patient.

This approach has advantages in that the use of a mesh layer allows one dimension of the sample chamber to be tightly controlled while also reducing the void volume, thereby reducing the volume of the test sample required. Woven mesh layers are generally fabricated from synthetic polymeric fibers of known diameter, typically nylon and polyester fibers. Nylon and polyester fibers are relatively hydrophobic and, consequently, meshes constructed from the untreated fibers are unsuitable for direct use for promoting transportation of the test sample in a biosensor.

U.S. Pat. No. 5,628,890 discloses the use of a surfactant-coated mesh layer in a biosensor for the purpose of wicking A fluorinated surfactant, "FLUORAD FC-170C" (3M Company, St. Paul, Minn.) is disclosed as a preferred surfactant in this system. Manufacture of the fluorinated surfactant FC-170C was terminated by the 3M Company because of concerns relating to its effect on the environment. Furthermore, the Environmental Protection Agency (EPA) has recently imposed restrictions on the manufacture and use of such surfactants and related substances in the United States. Similar fluorinated surfactants are still available from other manufacturers, but there is a legitimate concern that such materials may be withdrawn from the market in the future.

Accordingly, the surfactant "FLUORAD FC-170" needs to be replaced by an equally effective non-fluorinated surfactant, preferably one that is commercially available. A surfactant must fulfill the following requirements: long-term stability, ease of applying onto the mesh layer, in particular, applying by means of an aqueous solution. The Gower Handbook of Industrial Surfactants lists over 21,000 products.

Textile spin finishes are non-permanent coatings applied to fibers and yarns as emulsions in order to improve lubrication and prevent antistatic build-up during processing (Philip E. Slade, *Handbook of Fiber Finish Technology*, Marcel Dekker (1998)). Spreading of the spin finish emulsion on the surface of the fiber to achieve a uniform coating is promoted by the addition of surfactants to the formulation. This type of spreading is somewhat analogous to the situation with respect to biosensors, where a test sample of high surface tension, i.e., blood, is applied to a surfactant-coated mesh, where initial wetting occurs followed by subsequent spreading. However, an important difference is that the spin finish emulsion contains the surfactant and is applied to the untreated fiber whereas in the biosensor, the fiber is already coated with surfactant and a test sample (without surfactant) is applied to the coated fiber.

Silicone surfactants are available from a number of manufacturers, such as, for example, Dow Corning, OSi Specialities, Basildon Chemicals, Clariant, and Degussa. These surfactants are often used as additives (minor components) of fiber finishes, which are required during processing. They are added to finish formulations to promote wetting of the fiber with the hydrophobic finish and are not used to increase the hydrophilicity of the finished fiber. The fiber finish is required for lubrication and anti-static properties during processing. The prior art offers no specific guidance as to which surfactants will be effective as spreading agents when applied to mesh in biosensors.

The mechanics of the spreading/wicking process is complex. The coating emulsion requires a low surface tension to wet the surface of the fiber or yarn, but the wicking rate is greater at a high level of surface tension (Philip E. Slade, *Handbook of Fiber Finish Technology*, Marcel Dekker (1998), pg. 45-48). For example, fluorinated surfactants are known to be among the most effective at lowering surface tension but are reported to have "a considerable negative effect on wicking" (Wicking of Spin Finishes and Related Liquids into Continuous Filament Yarns, Y. K. Kamath, S. B. Hamby, H.-D. Weigmann and M. F. Wilde, *Textile Res. J.*, 1994, 64, 33-40). This finding is confirmed by spreading studies of surfactant solutions on Parafilm (K. P. Ananthapadmanabhan, E. D. Goddard and P. Chandar, *Colloids Surf,* 1990, 44, 281).

As stated previously, an important property of a biosensor is its long-term stability. The biosensor is required to function without any deterioration in performance for many months after manufacturing. Satisfactory performance requires the sample chamber to fill rapidly and uniformly over the shelf life of the product. Given that the coating of surfactant on the mesh layer is non-permanent and is necessary for adequate filling of the sample chamber, it follows that the surfactant itself must be chemically stable, while not undergoing excessive migration/diffusion from the mesh layer to other surfaces in the biosensor. Some loss of surfactant from the mesh layer to other hydrophobic surfaces (such as printed electrode tracks) is considered beneficial, because these surfaces will become more hydrophilic. Excessive loss will result in an unacceptable deterioration in wicking performance, leading ultimately to a catastrophic failure to fill. Surfactants having high molecular weight, which are either solids or viscous liquids, are expected to be less mobile and therefore more capable of providing durable spreading capability. However, such materials are expected to be less effective as spreading agents than those surfactants having lower molecular weights.

It is important to consider the interaction of the surfactant coated onto the mesh layer with adjacent layers in the biosensor. The surfactant may inhibit adhesion of other layers to the mesh layer. In addition, the mesh layer may be adhered to the electrode substrate by a screen-printed insulating ink, with which the surfactant could interact adversely. For example, the wet ink printed onto the surfactant-coated mesh layer may wick along the fibers, resulting in poor print definition.

It is not a simple case of applying any surfactant (or even specifically the most effective surfactants such as fluorinated surfactants) to a mesh layer of a biosensor to achieve rapid and uniform wicking of the applied test sample. Adequate models of the mechanics and dynamics of the spreading of surfactant solutions remain to be developed, largely because the phenomenon is so complex (Silicone Surfactants, Surfactant Science Series, Vol. 86, ed. Randall M. Hill, Marcel Dekker, 1999, pg. 303-310). Furthermore, there are other critical factors to consider when selecting a surfactant for specific use in a biosensor; many of these factors have not been considered previously in the literature.

In summary, a number of conflicting factors have to be balanced to obtain the optimal selection from an enormous range of commercially available surfactants. These factors include the ability to lower surface tension, coating stability, coating uniformity, stability of the surfactant, migration effects, adhesion inhibition effects, wicking speed, wicking uniformity, toxicity, and printing definition.

SUMMARY OF THE INVENTION

This invention provides a biosensor for determining the concentration of an analyte in a biological sample. The biosensor comprises a support, an arrangement of electrodes disposed on the support, a covering layer defining an enclosed space over the electrodes, an aperture in the covering layer for receiving a biological sample, and at least one mesh layer in the enclosed space between the covering layer and the electrodes, the at least one mesh layer coated with at least one silicone surfactant. The arrangement of electrodes preferably comprises a reference electrode or a counter electrode or both a reference and a counter electrode disposed on the support, and a working electrode disposed on the support, the working electrode spaced apart from the other electrode or electrodes on the support. The working electrode includes an enzyme capable of catalyzing a reaction involving a substrate for the enzyme and a mediator capable of transferring electrons between the enzyme-catalyzed reaction and the working electrode to create a current related to the activity of the enzyme and related to the concentration of the analyte in the sample. Alternatively, instead of an enzyme, the working electrode can include a substrate capable of catalyzing a reaction involving an enzyme for the substrate and a mediator capable of transferring electrons between the substrate-catalyzed reaction and the working electrode to create a current related to the activity of the substrate and related to the concentration of the analyte in the sample. The at least one layer of mesh has coated thereon a silicone surfactant. We have discovered that certain silicone surfactants are as effective as fluorinated surfactants with respect to performance of biosensors. These surfactants, when coated onto the mesh layer of the biosensor, are effective in facilitating the transport of aqueous test samples, such as blood, from the sample application zone to the reaction zone in the enclosed space, which is frequently referred to as a sample chamber. These surfactants are collectively referred to as silicone surfactants or siloxane surfactants. These surfactants are preferably non-ionic and may be coated onto a layer of polymeric mesh, such as, for example, nylon or polyester mesh.

The silicone surfactants combine a number of properties that are required for successful use in a biosensor. The overall performance of the silicone surfactants in the biosensor exceeds that of fluorinated surfactants, such as "FLUORAD FC-170C." Overall performance is based on the following parameters:

(a) speed of filling the sample chamber with the sample;
(b) uniformity of filling the sample chamber with the sample, i.e., straightness of filling front for the sample;
(c) shelf life (filling stability), preferably at least 18 months;
(d) minimization of adhesion failure between layers of the biosensor in contact with the surfactant;
(e) minimization of seepage of sample between layers of the biosensor;
(f) level of toxicity, i.e., non-toxicity being preferred;
(g) minimization of loss in printing definition of the ink layer that holds the mesh layer in place;
(h) transferability of liquid surfactant by contact to other surfaces in the biosensor to render them more hydrophilic.

Silicone surfactants are effective at reducing the surface tension of aqueous fluids, such as blood. Consequently, hydrophobic meshes coated with silicone surfactants are capable of being wetted by aqueous fluids, such as blood.

Rapid and uniform wicking of blood along the at least one mesh layer of a biosensor is desired for reproducible results. The time required to fill a sample chamber of a biosensor containing a mesh layer coated with a silicone surfactant exceeds that of a sample chamber of a biosensor containing a mesh layer coated with a fluorinated surfactant, such as "FLUORAD FC-170C." Wicking uniformity (straightness of moving liquid front) across mesh coated with silicone surfactants is superior to that across a mesh coated with a fluorinated surfactant, such as "FLUORAD FC-170C." Wicking/spreading rates vary according to the structure of the silicone surfactant. Silicone surfactants having low molecular weight are very efficient spreading agents, but lack the durability required for a biosensor. Durability must be balanced with spreading efficiency. For this reason, mixtures of silicone surfactants having different properties provide the best overall performance in a biosensor.

Biosensors having sample chambers containing at least one mesh layer coated with silicone surfactants have adequate long-term stability. The sample chambers continue to fill rapidly and uniformly for at least 18 months when stored at 30° C. A shelf life of longer than 18 months is not required for a biosensor. Long-term stability is desired so that a catastrophic failure is not observed near the end of shelf life.

Silicone surfactants are non-toxic and do not irritate the skin. In contrast, fluorinated surfactants are toxic. Silicone surfactants are freely available from a number of suppliers.

In some biosensor systems the surfactant-coated mesh layer is covered with a polymeric film to form the sample chamber. Good adhesion between the mesh layer/insulating layer and the polymeric film is important to ensure that the sample chamber remains intact and to specify the volume of the test sample required to fill the sample chamber. If adhesion were poor, the polymeric film could peel away or seepage of the test sample may occur between the polymeric film and the mesh layer/insulating layer at the edge of the sample chamber. Such seepage will increase the volume of sample required to fill the sample chamber. Silicone surfactants have no adverse effect on the adhesion between the layers forming the sample chamber.

In some biosensors, the surfactant-coated mesh layer is held in place by overprinting with a layer of insulating ink. The surfactant coating may promote wicking of the wet insulating ink along the fibers of the mesh layer, leading to a poor print definition. In extreme cases, the insulating ink could cover areas that are required to be exposed. Silicone surfactants are comparable to fluorinated surfactants such as "FLUORAD FC-170C" in providing satisfactory definition of the insulating ink layer in the biosensor, when applied to the mesh layer at an equivalent level.

The biosensors of this invention employ non-toxic and environmentally friendly silicone surfactants in place of fluorinated surfactants (e.g., "FLUORAD FC-170." The silicone surfactants act as wetting agents when applied to polymeric meshes, such as polyamide (e.g., nylon) and polyester (e.g., PET). The hydrophobic polyester and polyamide meshes, when coated with silicone surfactants, become hydrophilic, and hence promote the lateral transport/flow/wicking of an aqueous sample, such as blood, from a sample application zone to a reaction zone in a diagnostic assay device, such as a biosensor.

DETAILED DESCRIPTION OF THE INVENTION

Figure 1:
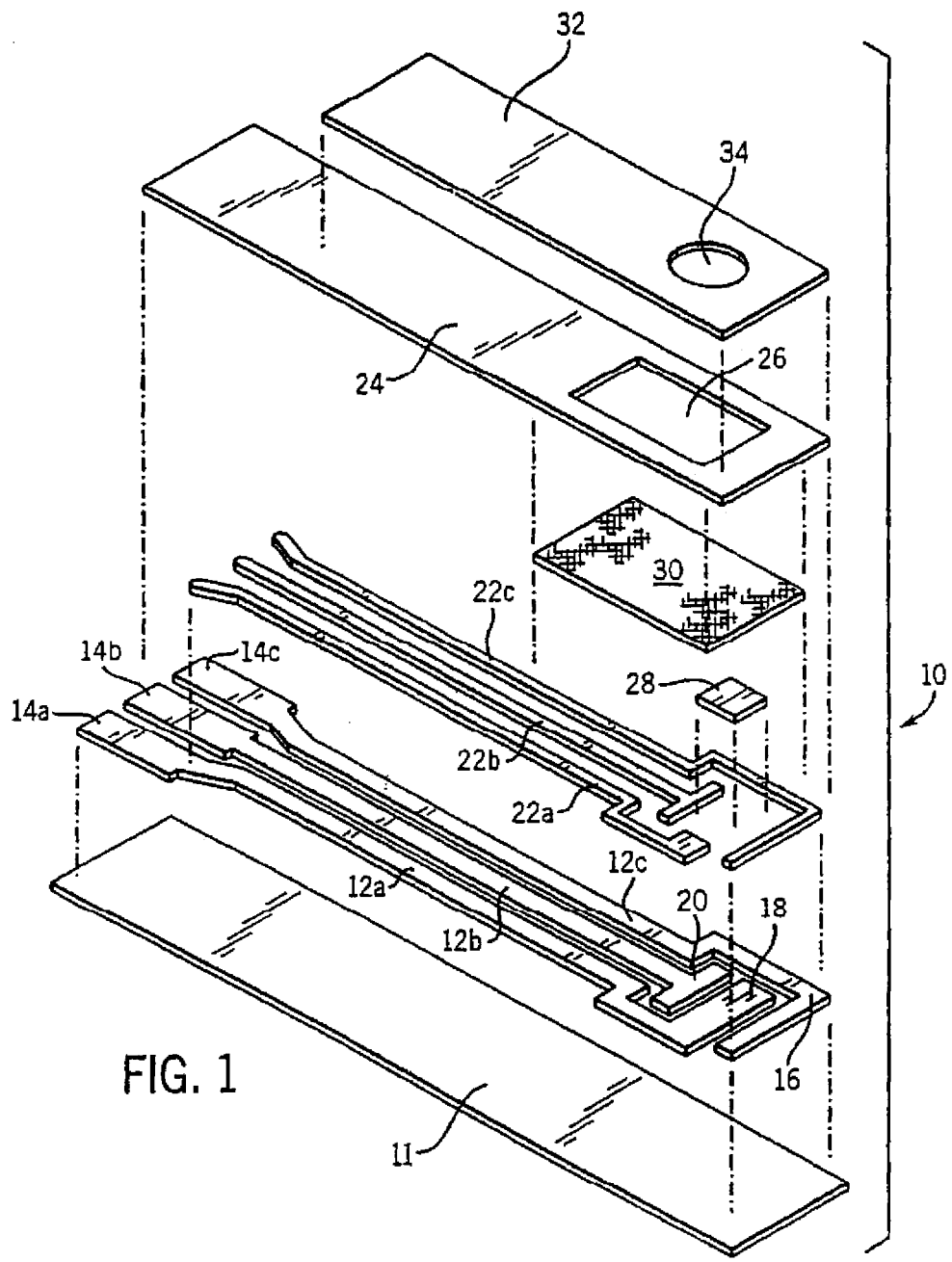
FIG. 1 is an exploded perspective view of a biosensor suitable for use in this invention.

As used herein, the terms "silicone" and "siloxane" are synonymous. The term "silicone" denotes a synthetic polymer $(R_n SiO_{(4-n)/2})_m$, where n=1 to 3, inclusive and m is equal to or greater than 2. A silicone contains a repeating silicon-oxygen backbone and has organic groups R attached to a significant proportion of the silicon atoms by silicon-carbon bonds. In commercial silicones most R groups are methyl; longer alkyl, fluoroalkyl, phenyl, vinyl, and a few other groups are substituted for specific purposes. Some of the R groups can also be hydrogen, chlorine, alkoxy, acyloxy, or alkylamino, etc. These polymers can be combined with fillers, additives, and solvents to result in products classed as silicones. See Kirk-Othmer Encyclopedia of Polymer Science and Technology, Volume 15, John Wiley & Sons, Inc. (New York: 1989), pages 204-209, 234-265, incorporated herein by reference.

This invention provides a biosensor for determining the concentration of an analyte in a biological sample. The biosensor comprises a support, a reference electrode or a counter electrode or both a reference and a counter electrode disposed on the support, a working electrode disposed on the support, the working electrode spaced apart from the other electrode or electrodes on the support, a covering layer defining a sample chamber over the electrodes, an aperture in the covering layer for receiving a sample, and at least one layer of mesh in the sample chamber between the covering layer and the electrodes on the support. The working electrode includes an enzyme capable of catalyzing a reaction involving a substrate for the enzyme and a mediator capable of transferring electrons between the enzyme-catalyzed reaction and the working electrode to create a current related to the activity of the enzyme and related to the concentration of the analyte in the sample. Alternatively, instead of an enzyme, the working electrode can include a substrate capable of catalyzing a reaction involving an enzyme for the substrate and a mediator capable of transferring electrons between the substrate-catalyzed reaction and the working electrode to create a current related to the activity of the substrate and related to the concentration of the analyte in the sample. The at least one layer of mesh has coated thereon at is least one silicone surfactant.

By applying certain silicone surfactants to the at least one layer of mesh, which is typically constructed of a hydrophobic polymeric material, the at least one layer of mesh is rendered hydrophilic and can be wetted by water and waterborne solutions such as blood. This treated mesh facilitates the transport/flow/wicking of aqueous reagents, such as blood, to a reaction zone covered by the at least one layer of mesh, where the active ingredients of the biosensor are located for a quantitative assay. Without aid of the at least one surfactant, it would be impossible to wet the reaction zone by the reagents alone.

Representative examples of classes of silicone surfactants suitable for use in this invention are illustrated below:

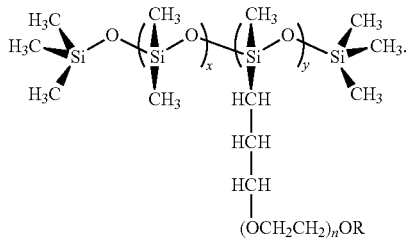

Formula I: molecular structure of a rake-type silicone surfactant; also called a comb or graft copolymer; R represents an end-capping group such as —H, —CH₃, or —COCH₃.

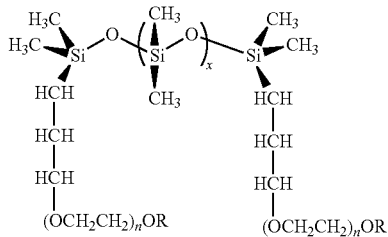

Formula II: molecular structure of ABA-type silicone surfactant; also called α-ω, or bolaform surfactant

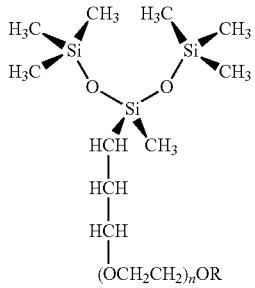

Formula III: molecular structure of a trisiloxane surfactant

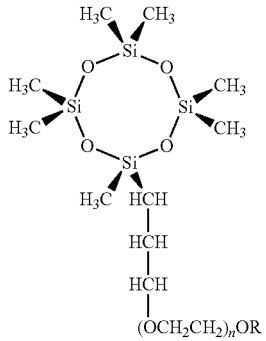

Formula IV: molecular structure of a cyclosiloxane surfactant

The silicone surfactants that are preferred for use in this invention have the general formula:

Formula V

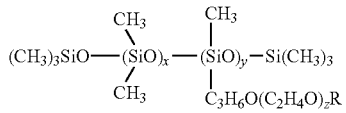

wherein:
z represents a value of 3 to 25, inclusive, preferably 3 to 15;
R represents hydrogen, an alkyl group, preferably having 1 to 4 carbon atoms, or an alkyl ester group, preferably having 1 to 4 carbons atoms in the alkyl portion, where, if y>1, each R can be the same or different on any given molecule, with R preferably being hydrogen or methyl;
x represents 0 up to a value in combination with y and z where the surfactant is not a liquid, x preferably being zero for the trisiloxane surfactants useful in surfactant mixtures;
y represents 1 up to a value in combination with x and z where the surfactant is not a liquid.

In general, non-ionic silicone surfactants comprise two structural units, a silicone group and a polyalkylene oxide chain; non-ionic silicones are preferred over cationic, anionic, or amphoteric silicones, because non-ionic surfactants allow the covering tape to readily adhere to the layer of coated mesh. The polyalkylene oxide chain preferably comprises ethylene oxide (EO) units or propylene oxide (PO) units or a mixture of the two. Varying the polyalkylene chain length and EO/PO ratio varies the properties of the surfactants. For example, increased water solubility is seen for those surfactants having a high ratio of EO to PO. In addition, surfactants having a short polyalkylene chain are known to be "superwetting agents." Furthermore, surfactants having high molecular weight are viscous liquids, which have good stability when coated onto polymeric fibers, due to a low mobility.

Surfactants that are particularly suitable for this invention have the following characteristics:
(a) Surface tension range: 20 to 35 mN/m
(b) Estimated viscosity range: 1 to 5000 cSt
(c) Estimated specific gravity range: 0.98 to 1.20
(d) Solubility or dispersibilty in water and alcohols: up to 10%.
(e) Cloud point: preferably >25° C. at 10% concentration in coating solution of choice (water/alcohol mixture)
(f) Molecular weight: number average molecular weight based on number of surfactants ranges from about 500 to about 30,000
(g) Additives: no additives are deliberately added beyond the manufacturer's formulation, which may contain additives or stabilizers or both
(h) Surfactant should be a liquid coating that can transfer to other surfaces by contact The silicone surfactant preferred for this invention has the trade name Dow Corning 193 Fluid, because it has a good balance of aqueous solubility, wetting ability, and stability. This silicone surfactant has a preferred rake-type structure (see the structures shown in Formulas I and V) and contains only EO with no PO. Dow Corning 193 Fluid has a molecular weight of approximately 2500.

The choice of a single surfactant for coating fibers of a mesh layer requires a compromise between various conflicting factors. However, a mixture of surfactants applied to the fibers of a mesh layer may achieve an enhanced effect, because a combination of "superwetting" agent and high molecular weight products can be used. A "superwetting" agent alone will have poor stability, and a surfactant having very high molecular weight will have poor wetting properties and aqueous solubility, but good stability.

The surfactant or mixture of surfactants is first dissolved in an organic is solvent (e.g., acetone), water, or a mixture of water and organic solvent (e.g., water/isopropanol) to yield a solution having a concentration in the range 0.01 to 10%, based on weight. The polymeric meshes are typically in a roll format and have various dimensions. Coating of the surfactant is achieved by continuously transporting the polymeric mesh from one end to the other through a bath of the solution of surfactant at a constant speed. A drying process is used to remove the solvent from the coating composition. In the drying process, temperatures of up to 130° C. can be used.

Silicone surfactants are environmentally friendly and non-toxic, as compared with fluorinated surfactants, such as "FLUORAD FC-170C", which are toxic and persistent in the environment. Silicone surfactants are at least equivalent to the fluorinated surfactants currently available, with respect to performance of current biosensor strips. The sample chambers fill rapidly and uniformly with blood over the shelf life of the strips. Silicone surfactants are manufactured by many companies; hence, there is no problem of shortage of suppliers, in contrast to fluorinated surfactants.

A stable, rapidly-fillable sample chamber containing a surfactant-coated mesh system for a biosensor can be obtained where through the use of a single liquid silicone surfactant of Formula V, where x ranges from 7 to 12, inclusive, y ranges from 3 to 5, inclusive, z ranges from 3 to 15, inclusive, R being hydrogen or methyl. Preferably, x ranges from 8 to 9, inclusive, y ranges from 3 to 4, inclusive, z ranges from 11 to 13, inclusive, R being hydrogen. A silicone surfactant having these values of x, y, and z is similar to Dow Corning 193 Fluid. Commercial surfactants typically have a range of x, y, and z values, whereby a distribution of molecular weights is obtained.

A stable, rapidly fillable sample chamber containing a surfactant-coated mesh system for a biosensor can be obtained through the use of a mixture of two silicone surfactants. Preferably, the mixture comprises a surfactant having high molecular weight having satisfactory properties with respect to stability of the biosensor and a surfactant having low molecular weight having satisfactory properties for rapid filling of the sample chamber. Most preferably, in the surfactant of high molecular weight (Formula V), x ranges from 8 to 9, inclusive, y ranges from 3 to 4, inclusive, z ranges from 11 to 13, inclusive, R being H, i.e., similar to Dow Corning 193 Fluid. Most preferably, in the surfactant having low molecular weight (Formula V), preferably a trisiloxane surfactant, x is 0, y is 1, z ranges from 3 to 15, inclusive, R is hydrogen, methyl, or acetate.

The weight fraction of the silicone surfactant having high molecular weight in the mixture preferably ranges from 1% to 99%, inclusive. The weight fraction of the silicone surfactant having low molecular weight in the mixture preferably ranges from 1% to 99%, inclusive. The most preferred weight fraction for the silicone surfactant having high molecular weight ranges from 50% to 99%, inclusive, and the most preferred weight fraction for the silicone surfactant having low molecular weight ranges from 1% to 50%, inclusive.

The coating weight of the surfactant on the layer of mesh preferably ranges from about 0.01% to about 8%, based on the weight of the mesh.

Preferably, a mixture of surfactants suitable for the present invention will have two components as described previously. However, mixtures of surfactants containing three or more silicone surfactants can be used to achieve optimal effects.

A biosensor strip 10 suitable for this invention is illustrated in FIG. 1. Referring to FIG. 1, an electrode support 11, preferably an elongated strip of polymeric material (e.g., polyvinyl chloride, polycarbonate, polyester, or the like) supports three tracks 12a, 12b, and 12c of electrically conductive ink, preferably comprising carbon. These tracks 12a, 12b, and 12c determine the positions of electrical contacts 14a, 14b, and 14c, a reference electrode 16, a working electrode 18, and a counter electrode 20. The electrical contacts 14a, 14b, and 14c are insertable into an appropriate measurement device (not shown). This type of biosensor is shown in U.S. Ser. No. 10/062,313, filed Feb. 1, 2002, now U.S. Pat. No. 6,863,800, incorporated herein by reference. While this illustration involves a biosensor having a working electrode, a reference electrode, and a counter electrode, it is not critical for a biosensor to have three electrodes. One electrode can be used to perform the functions of the reference electrode and the counter electrode. Auxiliary electrodes can be added for other purposes. What is required is an electrode arrangement comprising at least a working electrode and a reference electrode. A type of biosensor having a working electrode and a single electrode to perform the functions of the reference electrode and the counter electrode is shown in WO 99/19507, published 22 Apr. 1999, incorporated herein by reference.

Referring again to FIG. 1, each of the elongated portions of the conductive tracks 12a, 12b, and 12c can optionally be overlaid with a track 22a, 22b, and 22c of conductive material, preferably made of a mixture comprising silver particles and silver chloride particles. The enlarged exposed area of track 22b overlies the reference electrode 16. A layer of a hydrophobic electrically insulating material 24 further overlies the tracks 22a, 22b, and 22c. The positions of the reference electrode 16, the working electrode 18, the counter electrode 20, and the electrical contacts 14a, 14b, and 14c are not covered by the layer of hydrophobic electrically insulating material 24. This hydrophobic electrically insulating material 24 serves to prevent short circuits. The layer of hydrophobic electrically insulating material 24 has an opening 26 formed therein. This opening 26 provides the boundary for the reaction zone of the biosensor strip 10. Because this insulating material is hydrophobic, it can cause the sample to be restricted to the portions of the electrodes in the reaction zone. The working electrode 18 comprises a layer of a non-reactive electrically conductive material on which is deposited a layer 28 containing a working ink for carrying out an oxidation-reduction reaction. At least one layer of mesh 30 overlies the electrodes. This mesh layer 30 protects the printed components from physical damage. The mesh layer 30 also helps the sample to wet the electrodes by reducing the surface tension of the sample, thereby allowing it to spread evenly over the electrodes. A cover 32 encloses the surfaces of the electrodes that are not in contact with the electrode support 11. This cover 32 is a liquid impermeable membrane. The cover 32 includes a small aperture 34 to allow access of the applied sample to the underlying mesh layer 30.

The layer of working ink 28 is deposited on that portion of the electrically conductive material of the working electrode 18 where the oxidation-reduction reaction is to take place when a sample is introduced to the biosensor strip 10. The layer of the working ink 28 can be applied to the working electrode 18 as a discrete area having a fixed length. The working ink comprises reagent(s) that are responsive to the analyte of interest deposited on the non-reactive electrically conductive material. As used herein, the term "reagent(s)" means at least one reagent. Typical analytes of interest include, for example, glucose and ketone bodies. Typical non-reactive electrically conductive materials include, for example, carbon, platinum, palladium, and gold. A semiconducting material such as indium doped tin oxide can be used as the non-reactive electrically conductive material. In preferred embodiments, the working ink comprises a mixture of an oxidation-reduction (redox) mediator and an enzyme. Alternatively, instead of an enzyme, the working ink can contain a substrate that is catalytically reactive with an enzyme to be assayed. For example, when the analyte to be measured is glucose in blood, the enzyme is preferably glucose oxidase, and the redox mediator is preferably ferrocene or a derivative thereof. Other mediators that are suitable for use in this invention include a ferricyanide salt and a phenanthroline quinone or a derivative thereof. In the biosensor strips of this invention, the reagent(s) are preferably applied in the form of ink containing particulate material and having binder(s), and, accordingly, does not dissolve rapidly when subjected to the sample. In view of this feature, the oxidation-reduction reaction will occur at the interface of working electrode 18 and the sample. The glucose molecules diffuse to the surface of the working electrode 18 and react with the enzyme/mediator mixture.

In addition to being applied to the working electrode 18, a layer of the working ink can be applied to any of the other electrodes, when desired, as a discrete area having a fixed length.

The thickness of the layer of non-reactive electrically conductive material is determined by the method of applying the layer. In the case of a layer deposited by printing, e.g., screen-printing, the thickness of the layer typically ranges from about 10 micrometers to about 25 micrometers. In the case of a layer deposited by vapor deposition, the thickness of the layer typically ranges from about less than 1 micrometer to about 2 micrometers. The layer of the working ink 28 that has been deposited on the working electrode 18 typically has a dry thickness of from about 2 to about 50 micrometers, preferably from about 10 to about 25 micrometers. The actual dry thickness of the deposited layer of the working ink 28 will depend to some extent upon the technique used to apply the working ink. For example, a thickness of from about 10 to about 25 micrometers is typical for a layer of working ink applied by means of screen-printing.

The reference electrode 16 is typically formed by screen-printing a mixture comprising a mixture of silver and silver chloride on the electrode substrate 11. For materials to which such a mixture does not readily adhere, it is preferred to deposit a layer of carbon on the electrode support to act as a primer layer for the mixture. This mixture is often referred to as ink. The mixture typically has a carrier comprising an organic solvent. Alternatives to the mixture of silver and silver chloride include mixtures of Ag and AgBr, mixtures of Ag and AgI, and mixtures of Ag and $Ag_2O$. The printed layer associated with the reference electrode 16 extends to partially cover the track of the carbon layer associated with the reference electrode 16, where the printed layer extends into the reaction zone. It is preferred to cover parts of the tracks 12a, 12b, and 12c outside the reaction zone with the mixture of silver and the silver compound associated therewith, so that the total electrical resistance of each track is reduced. Because no current flows through the reference electrode 16, non-classical reference electrodes can be used as the reference electrode. These non-classical electrodes can be formed either by simply employing a conductive material, such as, for example, carbon, platinum, or palladium, as the reference electrode or by having the working ink deposited on the conductive material that forms the reference electrode. The reference electrode 16 preferably has equal or smaller dimensions compared to those of the working electrode 18.

If the working ink is deposited on a conductive material to form the reference electrode 16, the reagent(s) are deposited only on the portion of the electrode that is in the reaction zone to minimize the electrical resistance of the track 12c.

In the case of carbon being deposited to form the reference electrode 16 (i.e., an electrically conductive electrode without oxidation-reduction reagents), no additional material is required to be deposited on the surface of the reference electrode. The carbon can be doped with metal particles to increase the conductivity of the carbon.

Any electrically conductive material can be used to form the counter electrode 20. Preferred materials for forming the counter electrode 20 include, but are not limited to, platinum, palladium, carbon, gold, silver, and mixtures of silver and silver chloride (as in the reference electrode 16). In another embodiment, reagent(s) that form the working ink can be deposited on the conductive material of the counter electrode 20. If the working ink is deposited on a conductive material to form the counter electrode 20, the reagent(s) are deposited only on the portion of the electrode that is in the reaction zone to minimize the electrical resistance of the track 12b.

The dimensions of the counter electrode 20 are preferably equal to or greater than those of the reference electrode 16. It is preferred that the counter electrode 20 be of a size equal to or greater than the working electrode 18, though this preference is not required at low levels of current. In functional terms, the size of the reference electrode is not critical; the size of the working electrode is selected on the basis of signal to noise ratio desired; the size of the counter electrode is selected to minimize resistance to current flow.

The counter electrode 20 must be in electrical contact with the working electrode 18 during the measurement. When current flows through the counter electrode 20, the flow of electrons produces an electrochemical reaction (a reduction reaction) sufficient to allow the electrons to flow. The counter electrode 20 must be positioned at a sufficient distance from the working electrode 18 so that the reactive species generated at the counter electrode 20 do not diffuse to the working electrode 18.

The reaction zone can have total area ranging from about 1 $mm^2$ to about 20 $mm^2$, preferably about 5 $mm^2$. The area of the working electrode typically ranges from about 0.5 to about 5 $mm^2$, preferably about 1.0 $mm^2$. The reference electrode and the counter electrode typically have areas ranging from about 0.2 to about 4.0 $mm^2$, preferably about 0.5 $mm^2$.

The biosensor strip 10 typically has a width of from about 4.5 to about 6.5 mm. The electrode support 11 can be made from any material that has an electrically insulating surface, such as, for example, polyvinyl chloride, polycarbonate, polyester, paper, cardboard, ceramic, ceramic-coated metal, and blends of these materials (e.g., a blend of polycarbonate and polyester).

Electrically conductive material can be applied to the electrode support 11 by a deposition method such as screen-printing. This deposit of electrically conductive material forms the contact areas 14a, 14b, and 14c, which areas allow the analyte monitor to interface with the biosensor strip 10. The conductive material further provides electrical connections between the contact areas and the active reagent(s) deposited on the electrode(s) of the biosensor strip 10. The formulation for the electrically conductive material can be an air-dryable composition comprising carbon dispersed in an organic solvent. Alternative formulations include carbon dispersed in an aqueous solvent. Alternative electrically conductive materials that can be used in place of carbon include, but are not limited to, such materials as silver, gold, platinum, and palladium. Other methods of drying or curing the formulations containing the electrically conductive material include the use of infrared radiation, ultraviolet radiation, and radio frequency radiation. In an alternative method of application, the electrically conductive material can be deposited by means of a vapor deposition technique.

As stated previously, inks suitable for use in this invention can be screen-printed. Other ways of depositing the inks include drop coating, inkjet printing, volumetric dosing, gravure printing, flexographic printing, and letterpress printing. The electrically conductive portions of the electrodes are preferably screen-printed or deposited by means of sputtering or vapor deposition techniques. The reagents are preferably deposited by screen-printing or drop coating the formulations on the surface of the electrically conductive portion of the electrode. In the case of screen-printing, the reagents can be converted into particulate form wherein the particles contain carbon or silica, with carbon being preferred. In the drop coating formulation, the reagents can be mixed with a polymer (such as, for example, carboxy methyl cellulose, hydroxy ethyl cellulose, polyvinyl alcohol, etc.) solution to obtain a viscous solution, which is then dispensed on the area of interest. The inks can further include a polysaccharide (e.g., a guar gum, an alginate, locust bean gum, carrageenan, or xanthan), a hydrolyzed gelatin, an enzyme stabilizer (e.g., glutamate or trehalose), a film-forming polymer (e.g., a polyvinyl alcohol, hydroxyethyl cellulose, polyvinyl pyrrole, cellulose acetate, carboxymethyl cellulose, and poly(vinyl oxazolidinone), a conductive filler (e.g., carbon), a defoaming agent, a buffer, or combinations of the foregoing. Other fillers for the inks include, but are not limited to, titanium dioxide, silica, and alumina.

It is preferred that the length of the path to be traversed by the sample (i.e., the reaction zone) be kept as short as possible in order to minimize the volume of sample required. With respect to the biosensor strip described herein, the volume of sample required is preferably no greater than 5 microliters, and more preferably ranges from about 0.5 microliters to about 2.5 microliters. The maximum length of the reaction zone can be as great as the length of the biosensor strip. However, the corresponding increase in resistance of the sample limits the length of the reaction zone to a distance that allows the necessary response current to be generated. Positioning the electrodes in the manner described herein has the further advantage of preventing completion of a-circuit (and thus preventing detection of a response current) before the working electrode 18 has been completely covered by the sample.

As shown in FIG. 1, a mesh layer 30 overlies the electrodes. As stated previously, this mesh layer 30 protects the printed components from physical damage, and the mesh layer 30 also helps the sample to wet the electrodes by reducing the surface tension of the sample, thereby allowing it to spread evenly over the electrodes. Preferably, this mesh layer 30 extends over the entire length of the reaction zone, between and including the position at which the sample is introduced and the region where the electrodes are disposed. Preferably, this mesh layer 30 is constructed of woven strands of polyester. Alternatively, any woven or non-woven material can be used, provided that it does not occlude the surface of the electrode such that normal diffusion of the sample is obstructed. The thickness of the mesh is selected so that the depth of the sample is sufficiently low that a high sample resistance is produced. Preferably, the mesh layer 30 is not more than 150 µm in thickness. Preferably, the mesh layer 30 has a percent open area of about 35% to about 45%, a fiber count of about 40 per cm to about 60 per cm, a fiber diameter of about 70 µm to about 100 µm, an average mesh opening of about 67 to about 180 µm, and a thickness of from about 100 µm to about 160 µm. The diameter of the fiber can be outside the preferred range, e.g., about 10 µm to about 1000 µm. A particularly preferred mesh is PE130 HD mesh, available from Sefar (formerly ZBF), CH-8803, Ruschlikon, Switzerland.

The mesh layer 30 is coated with a surfactant. A surfactant coating is necessary only if the material of the mesh layer 30, itself, is hydrophobic (for example, nylon or polyester). If the material of the mesh layer 30 is hydrophilic, the surfactant coating can be used or can be omitted. A surfactant loading of from about 15 to about 20 µg/mg of mesh is preferred for most applications. The preferred surfactant loading will vary depending on the type of mesh layer and surfactant used and the sample to be analyzed. The preferred surfactant loading can be determined empirically by observing flow of the sample through the mesh layer 30 with different levels of surfactant.

The mesh layer 30 can be held in place by the layer of hydrophobic electrically insulating material 24. This layer of electrically insulating material 24 is preferably applied by screen-printing the ink over a portion of the periphery of the mesh layer 30. Together, the mesh layer 30 and the layers of hydrophobic electrically insulating material 24 surround and define a reaction zone 30 suitable for the sample to travel from the position at which the sample is introduced at one end of the strip towards the reference electrode 16, then toward the working electrode 18, and then toward the counter electrode 20. The hydrophobic electrically insulating material 24 impregnates the mesh layer 30 outside of the reaction zone 30. The hydrophobic electrically insulating material 24 thus defines the reaction zone 30 by preventing the sample from infiltrating the portions of the mesh layer 30 covered by the layers of hydrophobic electrically insulating material 24. A hydrophobic electrically insulating material 24 preferred for impregnating the mesh layers is "SERICARD" (Sericol, Ltd., Broadstairs, Kent, UK). Another preferred hydrophobic electrically insulating material is commercially available as "POLYPLAST" (Sericol Ltd., Broadstairs, Kent, UK).

A layer of dielectric ink can optionally be applied to cover the majority of the printed carbon and silver/silver chloride tracks. In this case, two areas are left uncovered, namely the electrical contact areas and the sensing areas in the reaction zone. This layer of dielectric ink serves to define the area constituting the reaction zone, and to protect exposed tracks from short circuit.

As shown in FIG. 1, a cover 32 encloses the surfaces of the electrodes that are not in contact with the electrode support 11. The cover 32 is a liquid impermeable membrane. This cover 32 can be a flexible tape made of polyester or similar material. The cover 32 includes a small aperture 34 to allow access of the applied sample to the underlying mesh layer 30. This cover 32 encloses the exposed surfaces of the working electrode 18, the reference electrode 16, and the counter electrode 20. Thus, the cover 32 maintains the available sample space over the electrodes at a fixed depth, which is equivalent to the thickness of the mesh layer 30. The positioning of this cover 32 ensures that the resistance of the sample is maintained at a high level.

The aperture 34 is positioned to overlie an end of the mesh area upstream of the reference electrode 16, such that the exposed mesh area beneath the aperture 34 can be used as a point of access or application for a liquid sample, whereby the sample contacts the reference electrode 16 before the sample contacts the working electrode 18 and the counter electrode 20. Of course, the aperture 34 must overlie an end of the mesh area that is not covered by the hydrophobic electrically insulating ink 30. The size of this aperture 34 is not critical, but it should be sufficiently large to allow sufficient volume of sample to pass through to the mesh layer 30. The aperture 34 should not be so large as to allow any portion of the liquid sample to contact any of the electrodes before contacting the mesh layer 30. The aperture 34 can be formed in the liquid impermeable cover 32 by any suitable method (e.g., die punching).

The liquid impermeable cover membrane 32 can be affixed to the biosensor strip by means of a suitable method of adhesion. Preferably, affixing is achieved by coating the underside of the flexible tape with a layer of hot melt glue, and then heat welding the tape to the surface of the layer of hydrophobic electrically insulating ink 24. The layer of hot melt glue typically has a coating weight of from about 10 to about 50 g/m², preferably from about 20 to about 30 g/m². Pressure sensitive adhesives or other equivalent methods of adhesion may also be used. Care should be taken when the tape is applied, because the heat and pressure applied to the tape layer can melt the "SERICARD" ink and can cause it to smear onto adjoining areas. Care should also be taken so that the tape does not cover the electrodes, the reaction zone, or the area where the sample is applied.

The upper surface of the liquid impermeable cover 32 can also be provided with a layer of silicone or other hydrophobic material. This additional layer serves to drive the applied sample onto the portion of exposed mesh layer 30 at the sample application point, thereby rendering the application of small volumes of sample much simpler.

In use, a biosensor strip 10 of this invention is connected, via electrode contacts 14a, 14b, and 14c, to a measuring device (not shown). A liquid sample is applied through aperture 34, and the sample moves along the reaction zone. The progress of the sample is sufficiently impeded by the mesh layer 30, thereby allowing the sample to form a uniform flow front. Air is displaced through the upper portion of the mesh layer 30 to and through the aperture 34. The sample first completely covers the working electrode 18 and the reference electrode 16, and only then approaches and covers the counter electrode 20, thereby completing the circuit and causing a response to be detected by the measuring device.

Measuring devices that are suitable for use in this invention include any commercially available analyte monitor that can accommodate a biosensor strip having a working electrode, a reference electrode, and a counter electrode. Such analyte monitors can be used to monitor analytes, such as, for example, glucose and ketone bodies. In general, such a monitor must have a power source in electrical connection with the working electrode, the reference electrode, and the counter electrode. The monitor must be capable of supplying an electrical potential difference between the working electrode and the reference electrode of a magnitude sufficient to cause the electrochemical oxidation of the reduced mediator. The monitor must be capable of supplying an electrical potential difference between the reference electrode and the counter electrode of a magnitude sufficient to facilitate the flow of electrons from the working electrode to the counter electrode. In addition, the monitor must be capable of measuring the current produced by the oxidation of the reduced mediator at the working electrode.

In this invention, the liquid sample is preferably a sample of whole blood. Alternatively, the liquid sample can be whole blood that has been filtered or treated to remove red blood cells or other hemocytes. Other biological samples, such as, for example, plasma, serum, urine, saliva, interstitial fluid, can be used.

The following non-limiting examples further illustrate this invention.

EXAMPLES

The surfactants used in the examples are listed in Table 1.

TABLE 1

| Identifier | Trade Name | Manufacturer | Type |
|---|---|---|---|
| S-20 | Span 20 | ICI | Sorbitan laurate ester |
| G2109 | Atlas G2109 | ICI | Lauric acid ethoxylate |
| PP822 | Cirrasol PP822 | ICI | Formulated surfactant mixture of mainly sorbitan ester, sorbitol ester, fatty acid ethoxylate |
| DC 193 | Dow Corning 193 | Dow Corning | Silicone surfactant containing ethylene oxide (EO) |
| DC 190 | Dow Corning 190 | Dow Corning | Silicone surfactant containing ethylene oxide (EO) and propylene oxide (PO) |
| FSO-100 | Zonyl FSO-100 | Dupont | Perfluoroalkylethoxylate |
| FSN-100 | Zonyl FSN-100 | Dupont | Perfluoroalkylethoxylate |
| FC-170C | Fluorad FC-170C | 3M | Perfluoroalkylsulfonamido oxyethylene adduct |
| OT-100 | Aerosol OT-100 | Cytec | Sodium diactyl sulfosuccinate |
| BC2213 | BC2213 | Basildon Chemicals | Trisiloxane surfactant containing ethylane oxide (EO) |
| BC2234 | BC2234 | Basildon Chemicals | Silicone surfactant containing ethylene oxide (EO) |
| PP3 | Duron PP3 | Hansa TexilChemie | Formulated mixture ot fatty acid ester, fatty acid ethoxylate(s), polyglycolic ether and amphoteric antistatics |

Example 1

The purpose of this example was to qualitatively assess the spreading ability of water onto a nylon mesh coated with a surfactant.

Various types of surfactants (TABLE 2) were coated onto strips of nylon mesh (15 mm wide, NY151, Sefar, Switzerland). Coating was performed by immersing the mesh in an aqueous acetone solution containing the given surfactant (0.1% w/w). The immersed mesh was then slowly withdrawn from the solution and dried in an oven at a temperature of 50° C. for two days. Two nylon mesh control samples, one uncoated and one coated with the surfactant FC-170C, were employed.

Short lengths of mesh coated with the various surfactants were sandwiched between a polyester sheet and a transparent polyester film by means of a tape having both major surfaces thereof coated with an adhesive (double-sided adhesive tape). This arrangement provided a model sample chamber with a height of approximately 180 to 190 μm, as measured by a micrometer.

Figure 2:
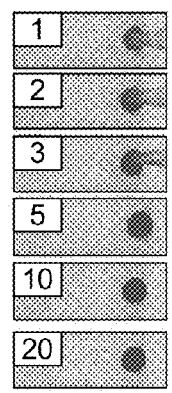
FIG. 2 is a series of video images (individual frames) showing water wicking into sample chambers of a model biosensor.
Figure 2:
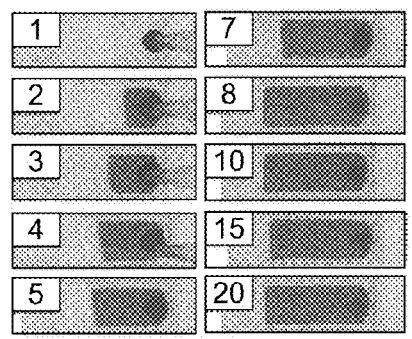
Figure 2:
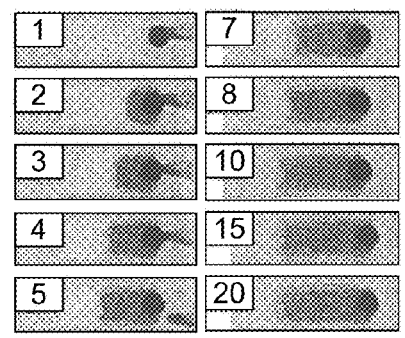

Colored water (10 μl) was applied by automatic pipette (Gilson) to the edge of the model sample chamber. The progress of the water as it was drawn into the sample chamber was recorded by a high-speed video camera at a speed of 16 frames per second. Examples of captured video images are shown in FIG. 2. The small number in the upper left corner of each frame represents the number of the frame from the introduction of the sample. The surfactant used was G2109. No spreading of water in the model sample chamber was seen for the uncoated control and the mesh coated with surfactants S-20, PP822, and FSO-100. These three surfactants were not included in further examples. In contrast, water did wick into model sample chambers containing mesh coated with surfactants FC-170C (control), G2109, PP3, DC 193, DC 190, and FSN-100.

TABLE 2

| Identifier | Trade Name | Spreading of water seen |
|---|---|---|
| S-20 | Span 20 | No |
| G2109 | Atlas G2109 | Yes |
| PP822 | Cirrasol PP822 | No |
| DC 193 | Dow Corning 193 | Yes |
| DC 190 | Dow Corning 190 | Yes |
| FSO-100 | Zonyl FSO-100 | No |
| FSN-100 | Zonyl FSN-100 | Yes |
| PP3 | Duron PP3 | Yes |
| FC-170C | Fluorad FC-170C (prior art control) | Yes |
| N/A | N/A (uncoated control) | No |

Example 2

The purpose of this example was to qualitatively assess the spreading ability of blood onto a nylon mesh coated with a surfactant.

Model sample chambers were constructed using nylon mesh from Example 1 that had been coated with the surfactants that were successful in spreading water (TABLE 3). Again, two nylon mesh control samples, one uncoated and one coated with the surfactant FC-170C, were employed.

Short lengths of mesh coated with the various surfactants were sandwiched between a polyvinyl chloride (PVC) sheet overprinted with a silver/silver chloride ink and a transparent polyester film by means of double-sided adhesive tape. This arrangement provided a model sample chamber having a height of approximately 180 µm, as measured by a micrometer. The use of a hydrophobic silver/silver chloride layer on the surface of one side of the model sample chamber was intended to reproduce more closely the environment within a typical commercially available sample chamber.

Figure 3:
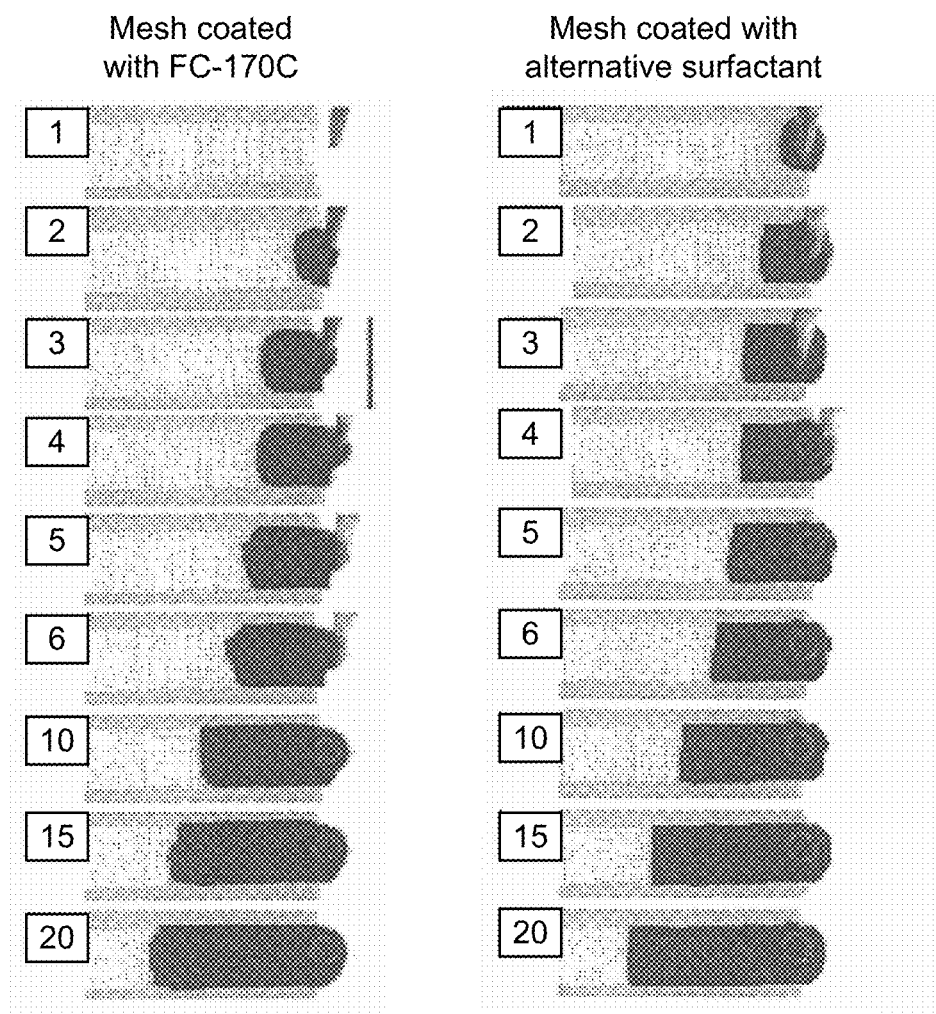
FIG. 3 is a series of video images (individual frames) showing blood wicking into sample chambers of a model biosensor.

Freshly drawn venous blood (10 µl) was applied by automatic pipette (Gilson) to the edge of the model sample chamber. The progress of the blood as it was drawn into the sample chamber was recorded by a high-speed video camera at a speed of 16 frames per second. Examples of captured video images are shown in FIG. 3. The small number in the upper left corner of each frame represents the number of the frame from the introduction of the sample. The surfactant used was G2109. No spreading of blood in the model sample chamber was seen for the uncoated control. Blood did wick into model sample chambers containing mesh coated with surfactants FC-170C (control), G2109, PP3, DC 193, DC 190, and FSN-100. However, the wicking speed for blood was observed to be slower than that recorded for water in Example 1. This result is expected because of the higher viscosity of blood relative to that of water.

TABLE 3

| Identifier | Trade Name | Spreading of blood seen |
|---|---|---|
| G2109 | Atlas G2109 | Yes |
| DC 193 | Dow Corning 193 | Yes |
| DC 190 | Dow Corning 190 | Yes |
| FSN-100 | Zonyl FSN-100 | Yes |
| PP3 | Duron PP3 | Yes |
| FC-170C | Fluorad FC-170C (prior art control) | Yes |
| N/A | N/A (uncoated control) | No |

Example 3

The purpose of this example was to qualitatively assess the spreading ability of blood onto a nylon mesh coated with surfactants, where the nylon mesh is incorporated into a biosensor having two layers of mesh.

Biosensors substantially similar to those described in U.S. Pat. No. 5,628,890, incorporated herein by reference, were constructed. The biosensors contained a working electrode, an electrode that performs as a reference electrode and a counter electrode, and a trigger electrode. The sample chamber of the biosensor contained two layers of nylon mesh, both of which were coated with surfactant. The layers of nylon mesh were designated NY64 and NY151, both supplied by Sefar (Switzerland). A dip-coating technique was used to coat separate rolls of each type of mesh with the various surfactants being evaluated. TABLE 4 shows the identity and amount of surfactant coated on each layer of mesh.

Figure 4:
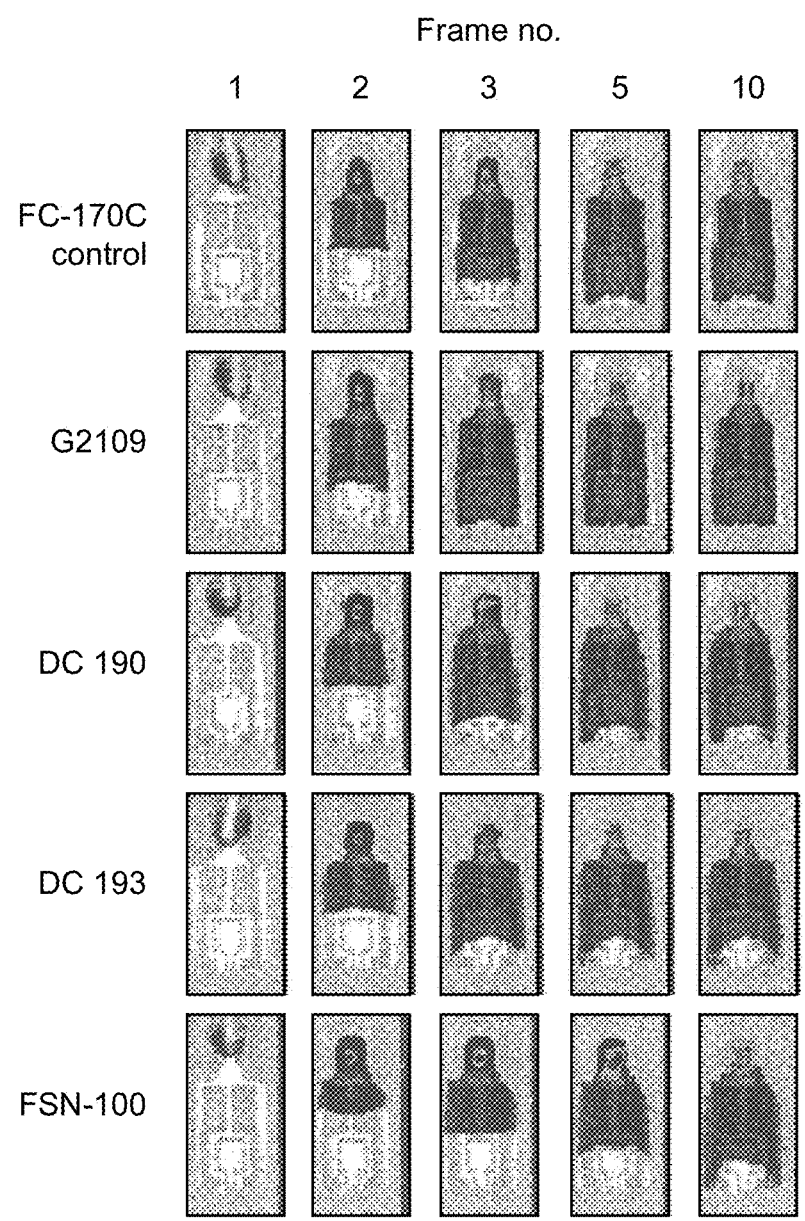
FIG. 4 is a series of video images (individual frames) showing blood wicking into sample chambers of a manufactured biosensor.

Freshly drawn venous blood (5 µl) was applied by automatic pipette (Gilson) to the edge of the sample chamber. The progress of the blood drawn into the sample chamber was recorded by a high-speed video camera at a speed of 16 frames per second. Examples of captured video images are shown in FIG. 4. Blood wicked into the sample chambers of the biosensors containing mesh coated with surfactants FC-170C (control), G2109, DC 193, DC 190, and FSN-100.

TABLE 4

| Identifier | Trade Name | Concentration of surfactant (% w/w) in NY64 coating bath | Concentration of surfactant (% w/w) in NY151 coating bath | Spreading of blood seen |
|---|---|---|---|---|
| G2109 | Atlas G2109 | 1% | 1% | Yes |
| DC 193 | Dow Corning 193 | 1% | 1% | Yes |
| DC 190 | Dow Corning 190 | 1% | 1% | Yes |
| FSN-100 | Zonyl FSN-100 | 1% | 1% | Yes |
| FC-170C | Fluorad FC-170C (prior art control) | 3.5% | 0.35% | Yes |

Example 4

The purpose of this example was to qualitatively assess the spreading ability of blood onto a nylon mesh coated with surfactants, where the nylon mesh is incorporated into a biosensor having two layers of mesh. The biosensors were stored 18 months prior to testing.

Biosensors of the type described in Example 3 were sealed in foil packets and stored at ambient temperature for 18 months. The biosensors were then tested with blood, and the average time of filling for the sample chambers were determined from recorded video sequences (TABLE 5).

In each run, a sample of freshly drawn venous blood was applied by automatic pipette (Gilson) to the edge of the sample chamber. The samples of blood were drawn from two donors. Each sample contained 10 µl of blood. For each type of surfactant, six biosensors were tested with blood samples from one donor and six biosensors were tested with blood samples from the other donor. The progress of the blood as it was drawn into the sample chamber was recorded by a high-speed video camera at a speed of 16 frames per second.

Sample chambers containing mesh coated with the surfactant G2109 were not stable and failed to fill with blood. The best performance with respect to filling was observed for the sample chambers containing mesh coated with surfactant DC 193. The filling speed for the sample chambers containing mesh coated with the surfactant DC 193 exceeded that of the sample chambers containing mesh coated with the surfactant FC-170C. Sample chambers utilizing mesh coated with the surfactant FSN-100 required almost twice as much time to fill as did sample chambers utilizing mesh coated with surfactant DC 193. Sample chambers containing mesh coated with the silicone surfactant DC 190 displayed filling performance comparable to that of sample chambers containing mesh coated with the surfactant FC-170C.

TABLE 5

| Identifier | Trade Name | Concentration of surfactant (% w/w) in NY64 coating bath | Concentration of surfactant (% w/w) in NY151 coating bath | Average time to fill sample chamber |
|---|---|---|---|---|
| G2109 | Atlas G2109 | 1% | 1% | Failed to fill |
| DC 193 | Dow Corning 193 | 1% | 1% | 2.7 sec |
| DC 190 | Dow Corning 190 | 1% | 1% | 3.4 sec |
| FSN-100 | Zonyl FSN-100 | 1% | 1% | 5.1 sec |
| FC-170C | Fluorad FC-170C (prior art control) | 3.5% | 0.35% | 3.2 sec |

Example 5

The purpose of this example was to qualitatively assess the spreading ability of blood onto a polyester mesh, where the polyester mesh is incorporated into a biosensor having one layer of mesh. The biosensors were stored 18 months prior to testing.

Biosensors substantially similar to that described in WO 99/19507, published 22 Apr. 1999, incorporated herein by reference, were constructed, with the exception that the sample chamber of the biosensor contained a single layer of polyester mesh coated with a surfactant. The biosensors contained a working electrode, an electrode that performs as a reference electrode and a counter electrode, and a trigger electrode. The sample was introduced at the end of the biosensor strip, not through an aperture in the cover layer. The layer of polyester mesh was PE130 mesh supplied by Sefar (Switzerland). A dip coating method was used to coat separate rolls of PE130 mesh with the various surfactants under evaluation (TABLE 6). Aqueous isopropanol solutions of surfactants were used for coating.

In each run, a sample of freshly drawn venous blood was applied by automatic pipette (Gilson) to the edge of the sample chamber. The samples of blood were drawn from two donors. Each sample contained 10 µl of blood. For each type of surfactant, six biosensors were tested with blood samples from one donor and six biosensors were tested with blood samples from the other donor. The progress of the blood as it was drawn into the sample chamber was recorded by a high-speed video camera at a speed of 16 frames per second.

Biosensors containing the surfactant G2109 were not stable and failed to fill. The best performance with respect to filling was observed for the sample chambers containing mesh coated with the surfactant DC 193. The filling speed for sample chambers containing mesh coated with the surfactant DC 193 exceeded that of the sample chambers containing mesh coated with the surfactant FC-170C. The sample chambers containing mesh coated with the surfactant DC 190 exhibited greater filling speed as compared with sample chambers containing mesh coated with the surfactant FC-170C, but were deemed unsuitable on the ground of very poor precision of electrode response. The surfactant DC 190 contains both EO and PO whereas the surfactant DC 193 contains only EO (TABLE 1).

TABLE 6

| Identifier | Trade Name | Concentration of surfactant (% w/w) in PE130 coating bath | Average time to fill sample chamber |
|---|---|---|---|
| G2109 | Atlas G2109 | 1% | Failed to fill |
| DC 193 | Dow Corning 193 | 1% | 1.9 sec |
| DC 190 | Dow Corning 190 | 1% | 2.4 sec |
| FSN-100 | Zonyl FSN-100 | 1% | 2.6 sec |
| FC-170C | Fluorad FC-170C (prior art control) | 3% | 2.9 sec |

Example 6

The purpose of this example was to quantitatively determine, by infrared (IR) spectroscopy, the quantity of silicone surfactant DC 193 coated onto nylon and polyester mesh. The stability of a biosensor is dependent upon the quantity of surfactant applied to the layer of mesh.

Various solutions of the surfactant DC 193 in water with approximately 5% isopropylalcohol (depending on concentration of the surfactant DC 193) were used as coating solutions. Polyester mesh (PE130, roll width of approximately 1 m) was passed through the coating solution and directed between two pinching rollers at a constant speed. The mesh was then dried at a temperature of 120° C. After the side edges of the roll of mesh were removed, the dried mesh was slit into rolls having a width of 14 mm. The coating process was performed by Sefar (Switzerland).

A length of polyester mesh (10 cm, PE130) was taken from a roll (width of 14 mm) and cut into two five (5) cm lengths. Each sample was weighed and then placed in a sealed glass test tube. Cyclohexane (5 ml; minimum purity 99.8%) was added to the test tube, and the test tube shaken for 15 minutes on an orbital shaker at a speed of 1400 rpm. The resulting solution was tested by FT-IR using a liquid sample cell having 1 mm path length having barium fluoride windows. The scan conditions were: 4 scans, 4 cm$^{-1}$ resolution, 1200 to 1050 cm$^{-1}$ range. The total peak area was calculated for the absorbance spectrum from 1145 to 1080 cm$^{-1}$. A calibration curve, obtained by measurement of known concentrations of the surfactant DC 193 in cyclohexane, was used to determine the quantity of the surfactant DC 193 in the extracted solution, and, consequently, the coating weight of the surfactant on the mesh sample.

The method described above can be used in a similar manner to determine the coating weight of the surfactant DC 193 on the nylon meshes NY64 and N151.

Figure 5:
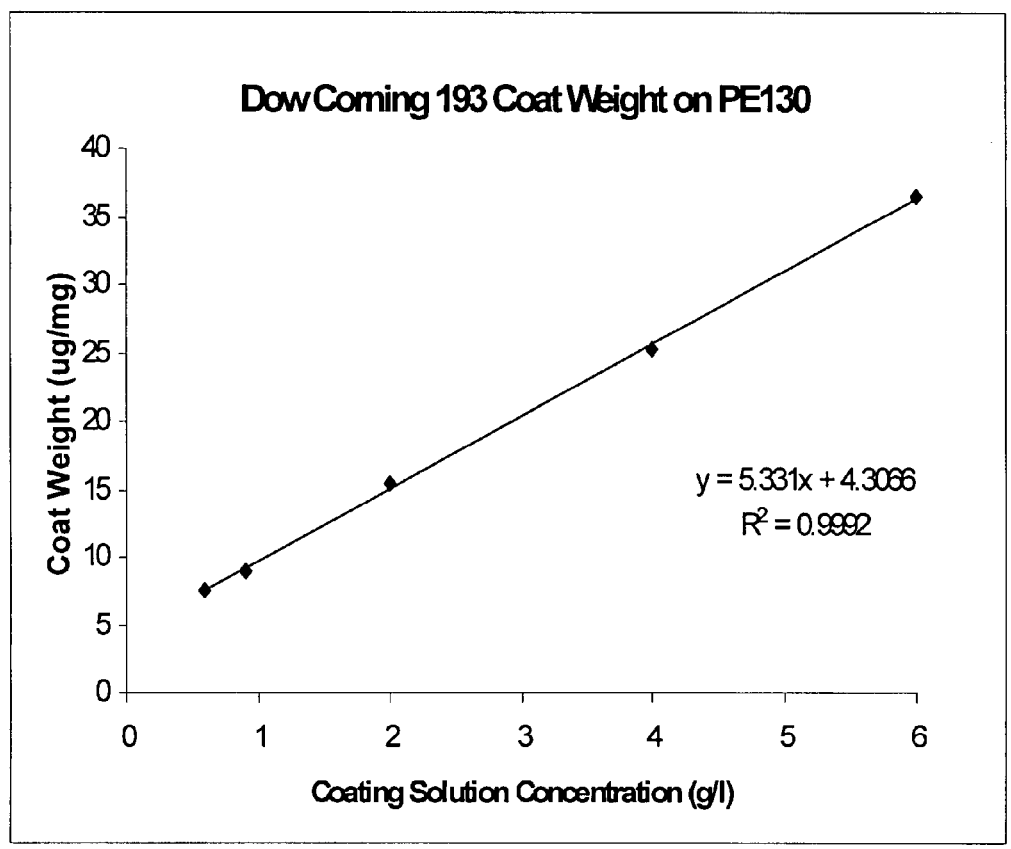
FIG. 5 is a graph showing coated weight of surfactant as a function of concentration of surfactant in coating solution.
Figure 6:
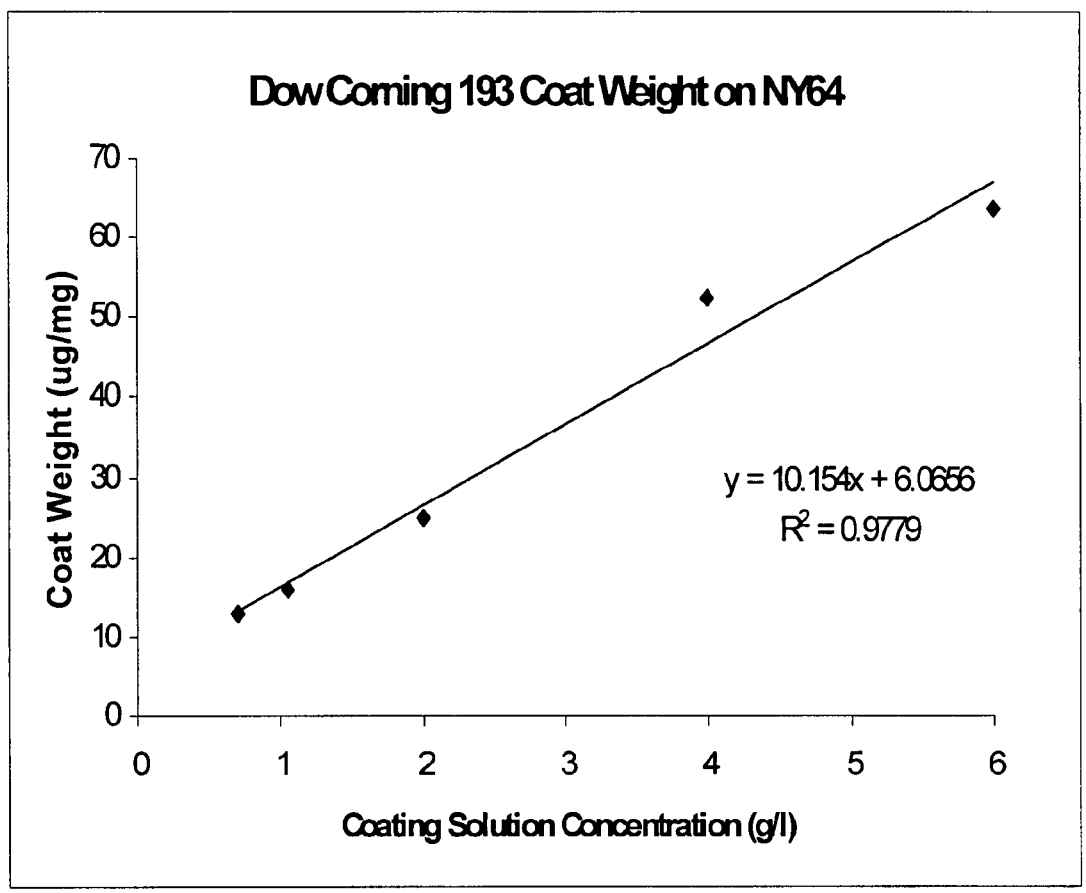
FIG. 6 is a graph showing coated weight of surfactant as a function of concentration of surfactant in coating solution.
Figure 7:
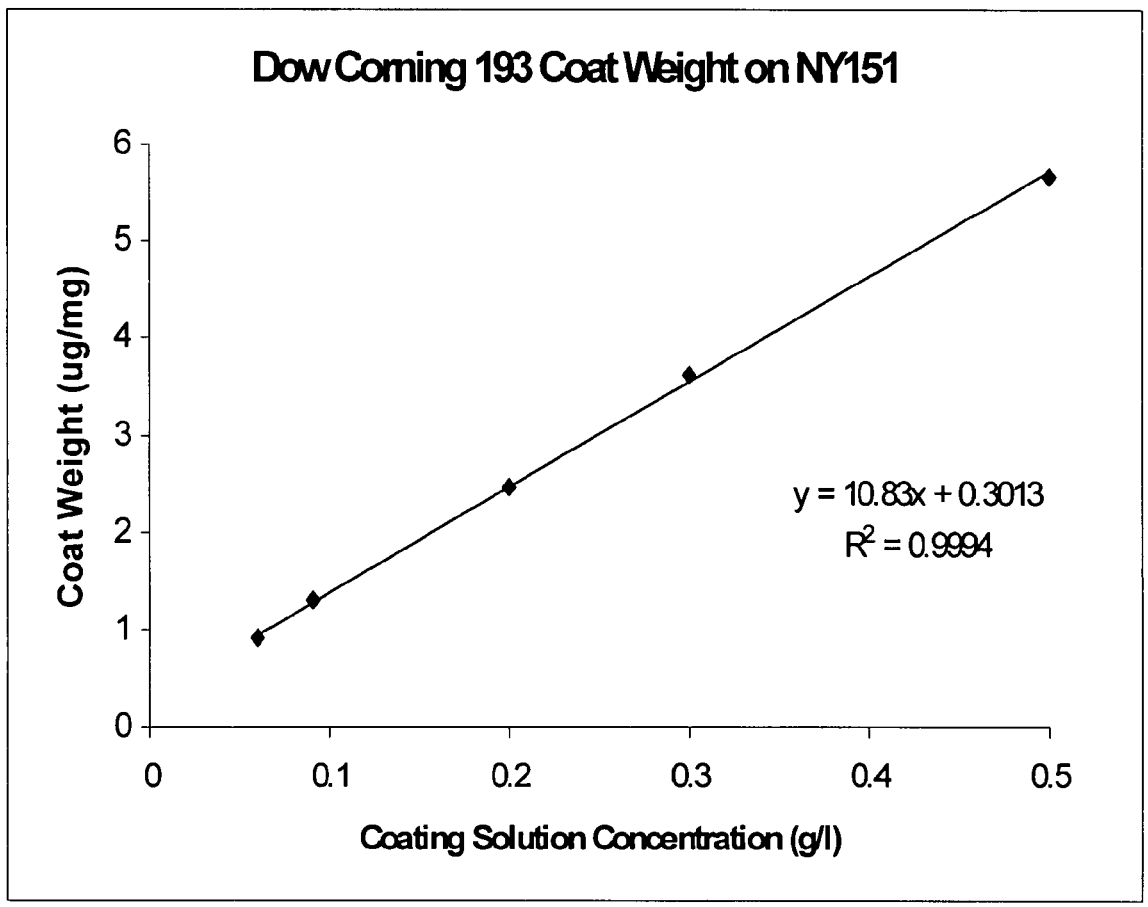
FIG. 7 is a graph showing coated weight of surfactant as a function of concentration of surfactant in coating solution.

A linear relationship was observed between the concentration of surfactant used in the coating solution and the weight of the surfactant coated on the polyester mesh PE130 (see FIG. 5) and on the nylon meshes NY64 (see FIG. 6) and NY151 (see FIG. 7), as determined by FT-IR and expressed in terms of µg of surfactant per mg of mesh.

Example 7

The purpose of this example was to determine the frequency of blood filling of biosensors having a single layer of mesh containing the surfactant DC 193 coated thereon, as a function of concentration of surfactant, storage temperature, and storage time.

Biosensors substantially similar to that described in Example 5 were used, except that the sample was introduced through an aperture punched through the biosensor. Various coating weights were used. The layer of polyester mesh was PE130 mesh, supplied by Sefar (Switzerland). Separate rolls of PE130 mesh were dip coated in aqueous isopropanol solutions of the surfactant DC 193.

The biosensors were packaged in foil and stored at ambient temperature (22° C.), 30° C., 40° C., and 50° C., for the purposes of the example. Ninety-six biosensors at each concentration of the surfactant DC 193 and at each storage temperature were tested at regular intervals to determine the percentage of the biosensors that could be filled with blood. In each run, a sample of freshly drawn venous blood was applied by automatic pipette (Gilson) to the edge of the sample chamber. The samples of blood were drawn from two donors. Each sample contained 10 µl of blood. Forty-eight biosensors were tested with blood samples from one donor and forty-eight biosensors were tested with blood samples from the other donor.

Figure 8A:
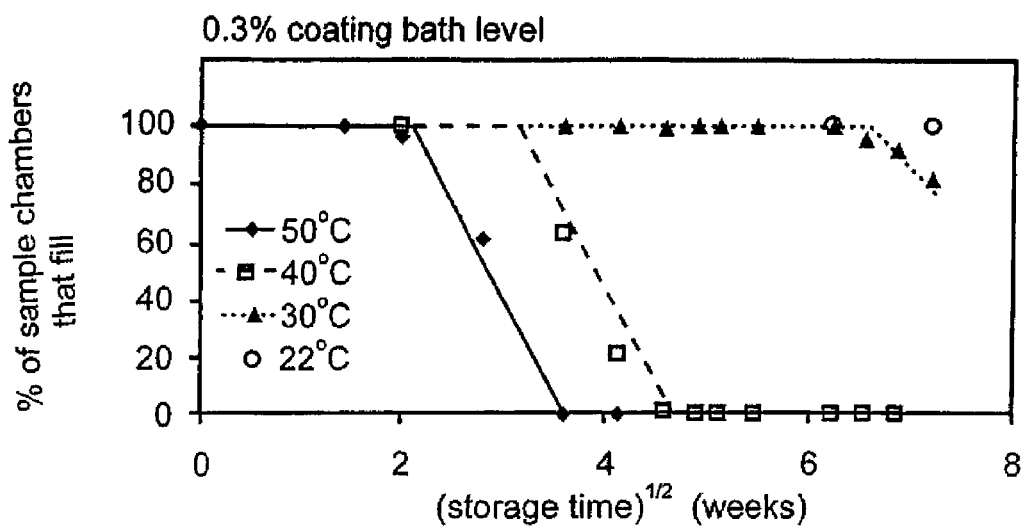
FIG. 8A is a graph showing percentage of biosensors that would fill as a function of storage time and storage temperature.
Figure 8B:
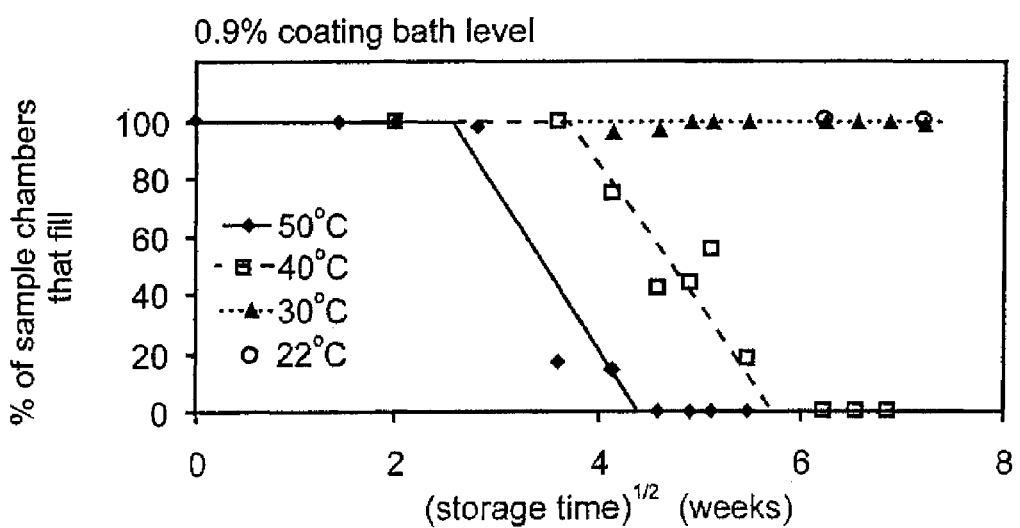
FIG. 8B is a graph showing percentage of biosensors that would fill as a function of storage time and storage temperature.
Figure 9:
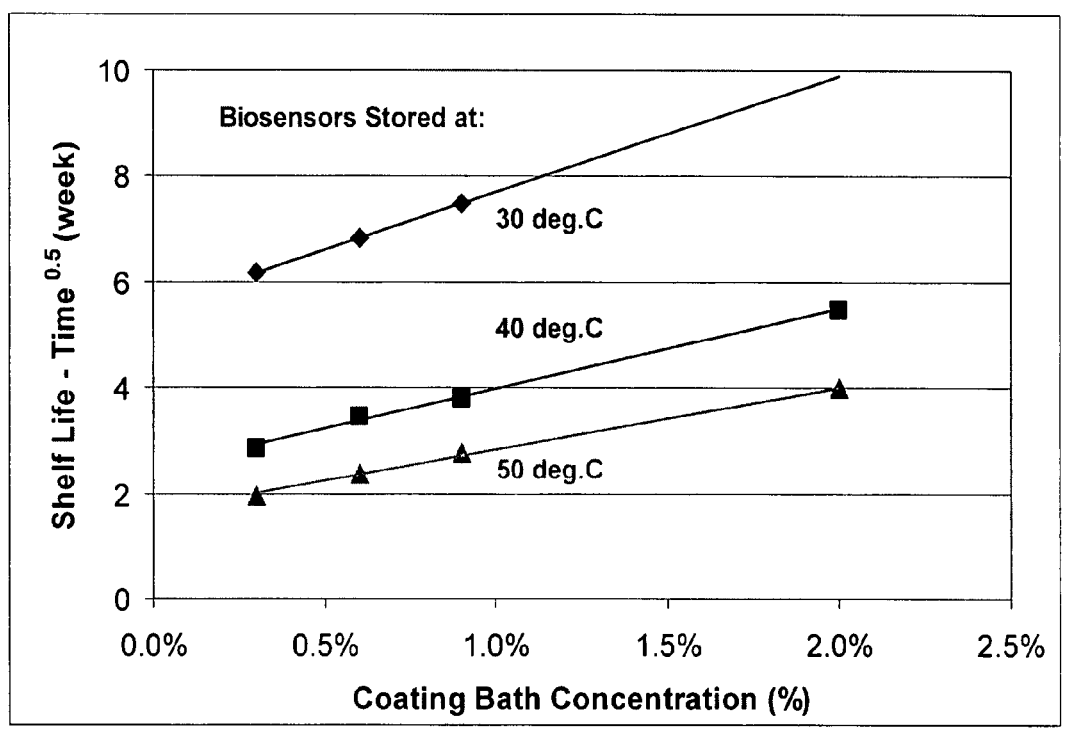
FIG. 9 is a graph showing shelf life of biosensors at a given storage temperature as a function of concentration of surfactant in coating bath.
Figure 10A:
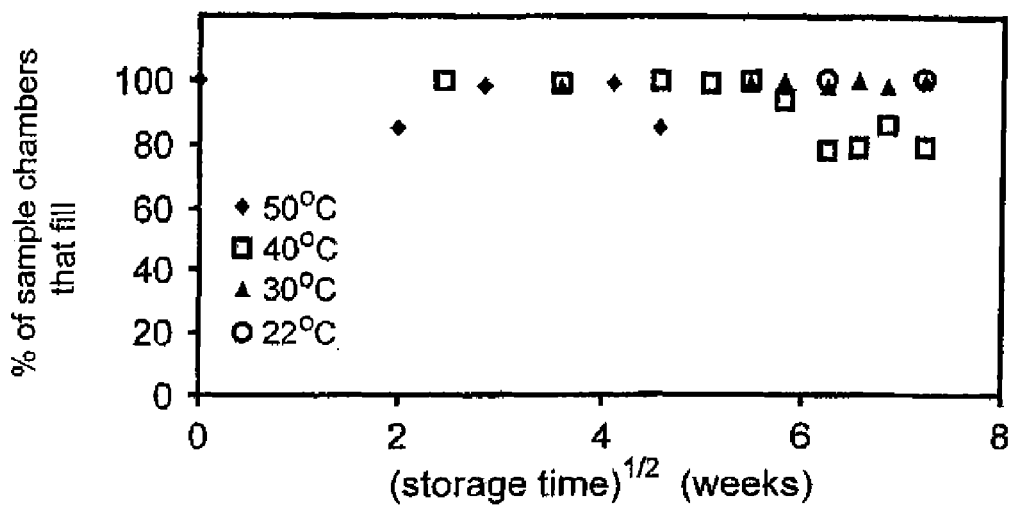
FIG. 10A is a graph showing percentage of sample chambers of biosensors that would fill as a function of storage time and storage temperature.
Figure 10B:
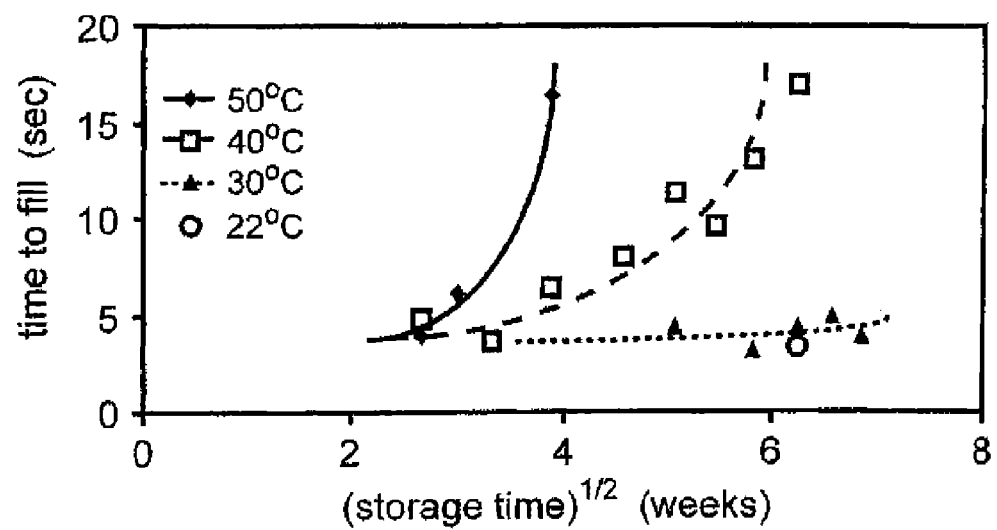
FIG. 10B is a graph showing the time to fill the sample chambers of biosensors as a function of storage time and storage temperature.
Figure 11A:
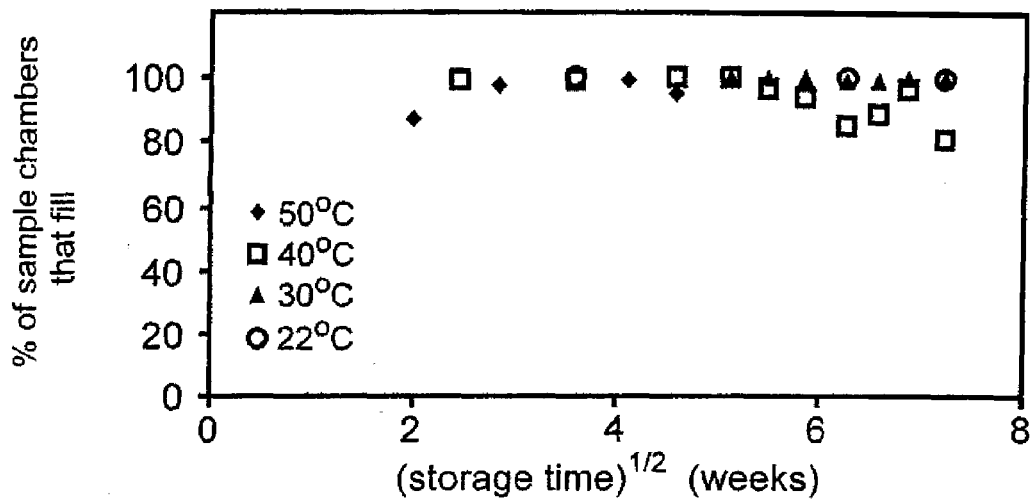
FIG. 11A is a graph showing percentage of sample chambers of biosensors that would fill as a function of storage time and storage temperature.
Figure 11B:
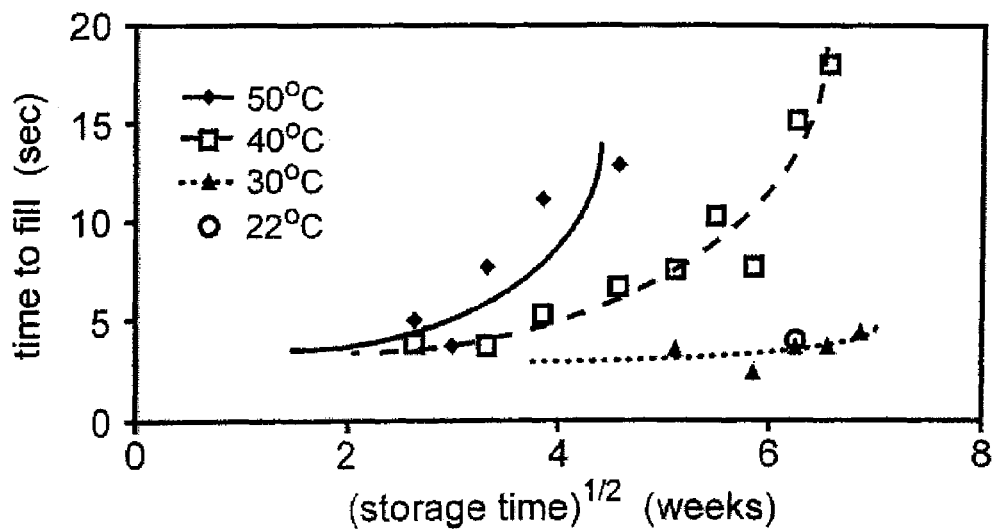
FIG. 11B is a graph showing time to fill the sample chambers of biosensors as a function of storage time and storage temperature.

The stability profiles of the biosensors were determined by plotting the percentage of the sample chambers of the biosensors that filled against the square root of the storage period (see FIG. 8A). Initially, 100% of the sample chambers filled with blood, but as storage time increased, this percentage declined until it was not possible to fill any sample chambers with blood. The stability profile can be enhanced by increasing the coating concentration of the surfactant DC 193 and decreasing the storage temperature. This enhancement is clearly seen in FIG. 8B. The shelf life required for the biosensor determines the minimum amount of the surfactant DC 193 that must be coated onto the layer of mesh. Biosensors containing polyester mesh coated with the surfactant FC-170C exhibited significantly more stability than did those biosensors having polyester mesh coated with the surfactant DC 193. For example, no failure of biosensors having mesh coated with FC-170C surfactant was observed at the storage temperature of 50° C. even after one year of storage. However, such stability is considerably in excess of that normally required (12 to 24 months at a storage temperature of 30° C.), and this requirement is achieved by coating the layer of mesh with the surfactant DC 193 at a sufficiently high concentration. Shelf life of the biosensor for a requirement of 100% filling at a storage temperature of 30° C. can be predicted from a plot such as that shown in FIG. 9.

Example 8

The purpose of this example was to determine the time of filling and the frequency of filling of biosensors having two layers of mesh in the sample chamber as a function of the concentration of surfactant, storage temperature, and storage time.

Biosensors of the type described in Example 3 were used. The sample chambers of the biosensors contained two layers of nylon mesh, both coated with the surfactant. The layers of nylon mesh were NY64 mesh and NY151 mesh, both supplied by Sefar (Switzerland). Separate rolls of each type of mesh were dip coated in a solution containing the surfactant DC 193. The concentration of the surfactant in the coating bath for the NY151 mesh was 0.09% DC 193. For the NY64 mesh, the concentrations of the surfactant in the coating bath were 0.35 and 1.05%.

The biosensors were packaged in foil and stored at ambient temperature (22° C.), 30° C., 40° C., and 50° C. for the purposes of the example. Ninety-six biosensors at each concentration of DC 193 at each storage temperature were tested at regular intervals to determine the percentage that can be filled with blood. In each run, a sample of freshly drawn venous blood was applied by automatic pipette (Gilson) to the edge of the sample chamber. The samples of blood were drawn from two donors. Each sample contained 10 µA of blood. Forty-eight biosensors were tested with blood samples from one donor and forty-eight biosensors were tested with blood samples from the other donor.

The stability profiles of the biosensors were assessed by plotting the percentage of the sample chambers that filled and the time of filling of the sample chambers as a function of the square root of storage time (see FIGS. 10A, 10B, 11A, 11B). Initially, 100% of the sample chambers filled with blood, but as the storage time increased, this percentage declined. Testing was terminated at 52 weeks. Time of filling was observed to increase as a function of the storage time and even more so as the storage temperature increased. The stability of filling was enhanced by increasing the coating concentration of the surfactant DC 193 and decreasing the storage temperature. Approximately 100% of the sample chambers of the biosensors filled in under five (5) seconds when stored at a temperature of 30° C. for a minimum of 12 months.

Example 9

The purpose of this example was to determine the time of filling of a biosensor having a single layer of mesh in the sample chamber as a function of concentration of surfactant and storage time at 50° C., with a variety of silicone surfactants coated onto the layer of mesh.

Biosensors similar to that described in Example 5 were used. The layer of polyester mesh was PE130 mesh supplied by Sefar (Switzerland). A dip coating method was used to coat separate rolls of PE130 mesh with the various surfactants being evaluated (TABLE 7). Aqueous isopropanol solutions of surfactants at concentrations of 1% w/w and 3% w/w were used for coating. A 50:50 mixture of the surfactants BC2213 and BC2234 was also evaluated.

The biosensors were packaged in foil and stored at a temperature of 50° C. for the purposes of the example. A sample of freshly drawn venous blood was applied by automatic pipette (Gilson) to the edge of the sample chamber. The samples of blood were drawn from two donors. Each sample contained 5 µl of blood. For each type of surfactant, six biosensors were tested with blood samples from one donor and six biosensors were tested with blood samples from the other donor. The progress of the blood as it was drawn into the sample chamber was recorded by a high-speed video camera at a speed of 16 frames per second.

TABLE 7

| Identifier | Trade Name | Manufacturer | Type of surfactant and approximate structure |
| --- | --- | --- | --- |
| DC 193 | Dow Corning 193 | Dow Corning | Silicone surfactant containing ethylene oxide (EO) $MD_9(D'E_{12}H)_4M$ |
| DC 190 | Dow Corning 190 | Dow Corning | Silicone surfactant containing ethylene oxide (EO) and propylene oxide (PO) $MD_{10}(D'E_{18}P_{18}H)_4M$ |

TABLE 7-continued

| Identifier | Trade Name | Manufacturer | Type of surfactant and approximate structure |
|---|---|---|---|
| FC-170C | Fluorad FC-170C (prior art control) | 3M | Perfluoroalkylsulfonamido oxyethylene adduct $C_8F_{17}SO_2N(E)(CH_2CH_2O)_n$-H |
| BC2213 | BC2213 | Basildon Chemicals | Trisiloxane surfactant containing ethylene oxide (EO) $M(D'E_{12}H)_4M$ |
| BC2234 | BC2234 | Basildon Chemicals | Silicone surfactant containing ethylene oxide (EO), methyl-capped $MD_9(D'E_{12}Me)_4M$ |

The standard nomenclature for silicone surfactants is used, where:

M represents $(CH_3)_3SiO$

D represents $(CH_3)_2SiO$

D' represents $(CH_3)SiO$ substituted with an EO or EO/PO polymeric chain linked with a $C_3H_6$ group. The polymer chain is terminated with a group R, which can be hydrogen, alkyl (preferably methyl), ester (preferably acetate)

E represents ethylene oxide (EO)

P represents propylene oxide (PO)

Figure 12:
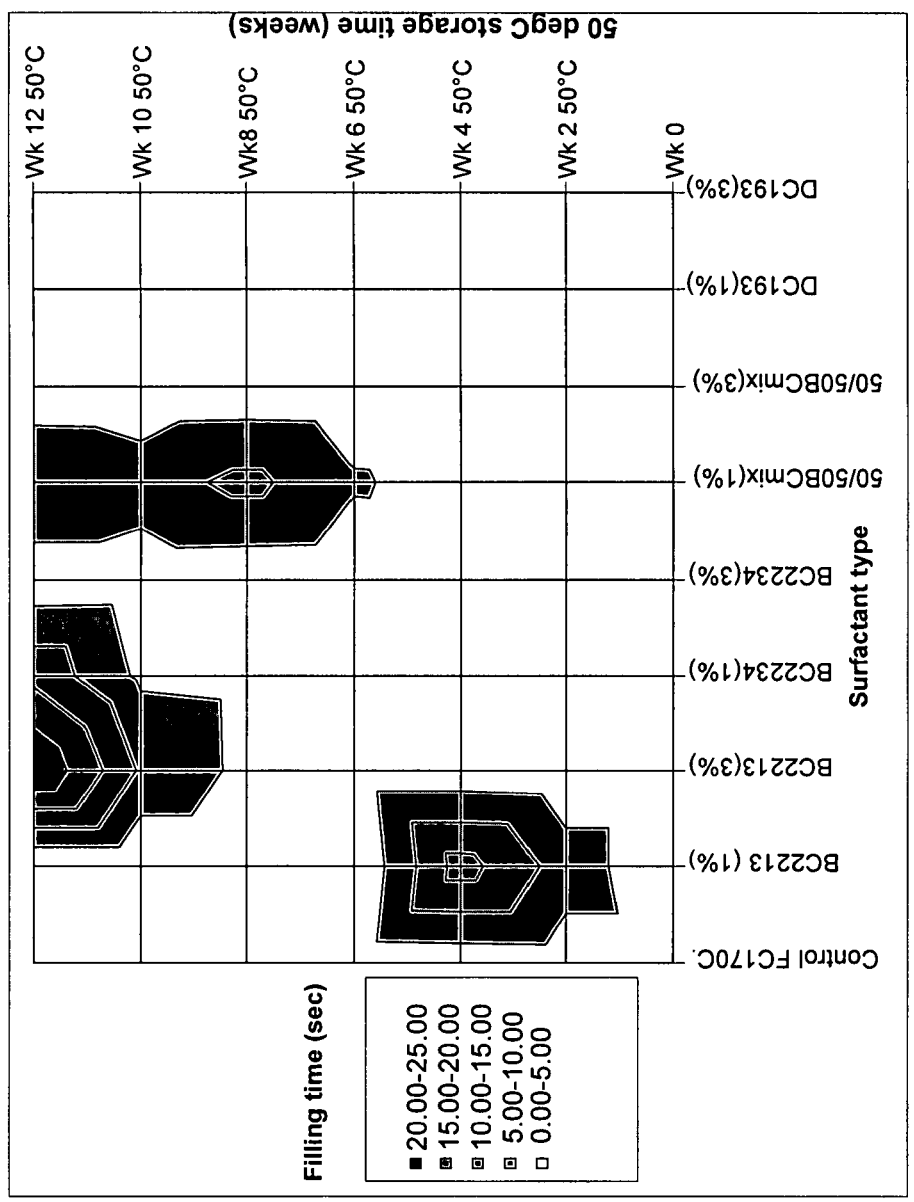
FIG. 12 is a contour plot showing variation in time of filling of a biosensor having a single mesh layer as a function of both the type of surfactant used and the storage time, where storage temperature was 50° C.

For example:

$MD_x(D'E_yR)_zM$ represents $(CH_3)_3SiO-((CH_3)_2SiO)_x-[CH_3SiO-\{C_3H_6-(C_2H_4O)_y-R\}]_z-OSi(CH_3)_3$ The average time of filling was calculated for biosensors containing different types of surfactants as a function of storage time (0-12 weeks) at a temperature of 50° C. The resulting data is shown in FIG. 12.

Stability failure points for the biosensors are indicated by large increases in time of filling. Stability failure was observed for 1% BC2213, 3% BC2213 and 1% BC2213 (50%)/BC2234 (50%). Increased stability can be brought about by increasing the weight of surfactant on the mesh layer (compare 3% BC2213 versus 1% BC2213). The stability of the silicone surfactants follows the approximate order from the greatest to the lowest:

[FC-170C (control)]>DC 193>C2234>BC2234 (50%)/BC2213 (50%)>BC2213

The low molecular weight trisiloxane surfactant BC2213 is the least stable, but a mixture of BC2213 with BC2234 exhibits increased stability.

TABLE 8 compares initial time of filling for biosensors containing the polyester mesh coated with various silicone surfactants with the initial time of filling of biosensors containing the polyester mesh coated with surfactant FC-170C. The time of filling follows the approximate order from lowest to greatest:

BC2213>BC2234~BC2234 (50%)/BC2213 (50%)>DC 193>FC-170C (control)

The time of filling for all the sample chambers containing mesh coated with silicone surfactants are lower than those for sample chambers containing the mesh coated with the surfactant FC-170C (control). The trend for time of filling is the converse of that seen for filling stability. Mixtures of silicone surfactants can provide the best compromise of filling speed and stability, e.g., a mixture of the surfactants BC2213 (rapid filling and poor stability) and BC2234 or DC 193 (slow filling and good stability).

TABLE 8

| Identifier | Concentration of coating bath for PE130 (% w/w) | Average time to fill sample chamber at t = 0 weeks |
|---|---|---|
| DC 193 | 1% | 1.60 sec |
| DC 193 | 3% | 1.93 sec |
| FC-170C | 3% | 2.25 sec |
| BC2213 | 1% | 1.03 sec |
| BC2213 | 3% | 1.17 sec |
| BC2234 | 1% | 1.18 sec |
| BC2234 | 3% | 1.07 sec |
| BC2213 (50%)/BC2234 (50%) | 1% | 1.22 sec |
| BC2213 (50%)/BC2234 (50%) | 3% | 1.12 sec |

Example 10

The purpose of this example was to qualitatively assess the adhesion of a polyester film and an insulating ink to a layer of nylon mesh coated with various surfactants in a biosensor having two layers of mesh.

Biosensors of the type described in Example 3 were used. The sample chambers of the biosensors contained two layers of nylon mesh, both coated with a surfactant. The layers of nylon mesh were NY64 and NY151, supplied by Sefar (Switzerland). The surfactants (G2109, DC 190, DC 193, FSN-100 and FC-170C), listed in TABLE 4, were included in this example, along with the anionic surfactant Aerosol OT-100 (listed in TABLE 1). The biosensors were assessed for any compatibility or adhesion problems or both between the various surfactants and any other materials.

In U.S. Pat. No. 5,628,890, the surfactant-coated mesh layer was held in place by overprinting with a layer of insulating ink (Sericard, commercially available from Sericol, Broadstairs, UK). The surfactants listed in TABLE 4 (G2109, DC 190, DC 193, FSN-100 and FC-170C) were compatible with the insulating ink. The polar anionic surfactant OT-100 was incompatible with the organic ink, with the result that it was not possible to adhere mesh coated with that surfactant to the surface of the electrode. For this reason, the surfactant OT-100 was rejected and no further work was carried out with it.

Figure 13A:
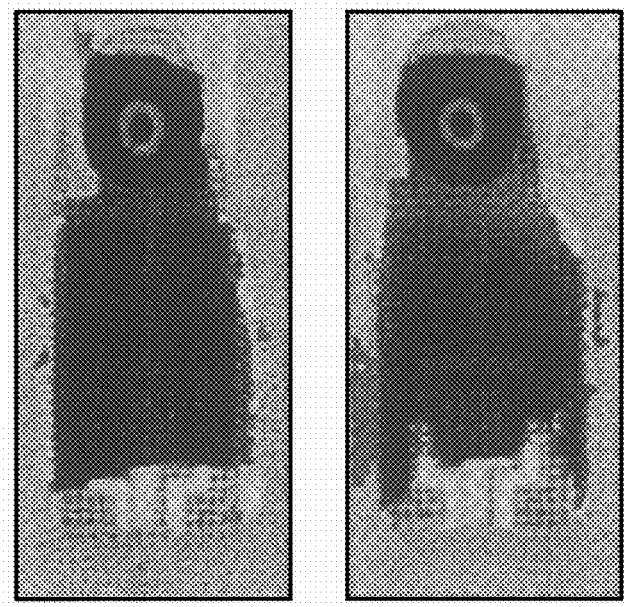
FIG. 13A are video images showing sample chambers of biosensors having two mesh layers filled with blood. The biosensors were stored at ambient temperature and the surfactants were DC 193 and FSN-100.
Figure 13B:
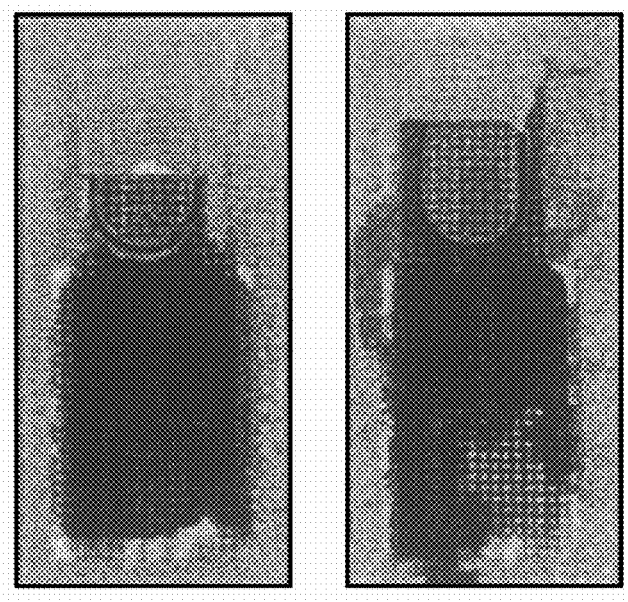
FIG. 13B are video images showing sample chambers of biosensors having two mesh layers filled with blood. The biosensors were stored at 40° C. for four weeks and the surfactants were DC 193 and FSN-100.

The surfactant-coated mesh layer also came into contact with a top layer of polyester film in those biosensors constructed according to U.S. Pat. No. 5,628,890. It is necessary to provide good adhesion between the polyester film and the surfactant-coated mesh where the sides of the sample chamber of the biosensor are formed. If good adhesion is not provided, the blood in the sample chamber may seep between the polyester film and the mesh that is being held in place by the insulating ink at the edge of the biosensor. The consequences of such seepage are that (1) the volume of blood required by the biosensor will be increased, and (2) the blood is not contained within the sample chamber, which may cause trouble with handling. The surfactants listed in TABLE 4 (G2109, DC 190, DC 193, and FC-170C), with the exception of FSN-100 provided biosensors wherein the polyester film adhered sufficiently to the insulating layer with little or no seepage of blood. The surfactant FSN-100 yielded biosensors having poorly adhering polyester film, as demonstrated in FIGS. 13A and 13B. The surfactant DC 193 performed well in this respect.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for making an electrochemical sensor, the method comprising:
    applying a working electrode and a counter electrode to the surface of a substrate;
    applying a mesh layer on top of the working and counter electrodes, the mesh layer coated with at least one silicone surfactant, wherein the at least one silicone surfactant comprises a mixture of silicone surfactants.

2. The method according to claim 1, wherein the mixture of silicone surfactants comprises a high molecular weight silicone surfactant and a low molecular weight silicone surfactant.

3. The method of claim 2, wherein the high molecular weight silicone surfactant and the low molecular weight silicone surfactant have the formula:

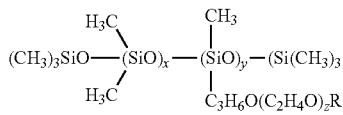

wherein x ranges from 8 to 9, inclusive, y ranges from 3 to 4, inclusive, z ranges from 11 to 13, inclusive, and R being hydrogen for the high molecular weight silicone surfactant; and x is 0, y is 1, z ranges from 3 to 15, inclusive, and R is hydrogen, methyl, or acetate for the low molecular weight silicone surfactant.

4. The method of claim 2, wherein the weight fraction of the high molecular weight silicone surfactant in the mixture ranges from 1% to 99%, inclusive.

5. The method of claim 2, wherein the weight fraction of the low molecular weight silicone surfactant in the mixture ranges from 1% to 99% inclusive.

6. The method of claim 1, wherein the method further comprises applying a working ink on top of the working electrode, the working ink comprising an analyte responsive enzyme and a mediator.

7. The method of claim 6, wherein the analyte responsive enzyme is selected from the group consisting of glucose oxidase, glucose dehydrogenase and 3-hydroxybutyrate dehydrogenase.

8. The method of claim 1, wherein the method comprises applying a single layer of mesh on top of the working and counter electrodes.

9. The method of claim 1, wherein the method comprises applying two or more layers of mesh on top of the working and counter electrodes.

10. The method of claim 1, wherein the at least one mesh layer is less than 150 microns in thickness.

11. The method of claim 1, wherein the method further comprises applying a cover layer on top of the mesh layer to define an enclosed space over the electrodes, wherein the mesh layer is positioned in the enclosed space.

12. A method for making an electrochemical sensor, the method comprising:
    applying a working electrode and a counter electrode to the surface of a substrate;
    applying a mesh layer on top of the working and counter electrodes, the mesh layer coated with at least one silicone surfactant, wherein the at least one silicone surfactant comprises a trisiloxane surfactant.

13. The method of claim 12, wherein the method further comprises applying a working ink on top of the working electrode, the working ink comprising an analyte responsive enzyme and a mediator.

14. The method of claim 13, wherein the analyte responsive enzyme is selected from the group consisting of glucose oxidase, glucose dehydrogenase and 3-hydroxybutyrate dehydrogenase.

15. The method of claim 12, wherein the method further comprises applying a cover layer on top of the mesh layer to define an enclosed space over the electrodes, wherein the mesh layer is positioned in the enclosed space.

16. A method for making an electrochemical sensor, the method comprising:
    applying a working electrode and a counter electrode to the surface of a substrate;
    applying a mesh layer on top of the working and counter electrodes, the mesh layer coated with at least one silicone surfactant, wherein the at least one silicone surfactant comprises a cyclosiloxane surfactant.

17. The method of claim 16, wherein the method further comprises applying a working ink on top of the working electrode, the working ink comprising an analyte responsive enzyme and a mediator.

18. The method of claim 17, wherein the analyte responsive enzyme is selected from the group consisting of glucose oxidase, glucose dehydrogenase and 3-hydroxybutyrate dehydrogenase.

19. The method of claim 16, wherein the method further comprises applying a cover layer on top of the mesh layer to define an enclosed space over the electrodes, wherein the mesh layer is positioned in the enclosed space.

* * * * *